(12) United States Patent
Wang et al.

(10) Patent No.: US 11,254,902 B2
(45) Date of Patent: Feb. 22, 2022

(54) CELL CULTURE MODULE, CELL CULTURE SYSTEM AND CELL CULTURE METHOD

(71) Applicant: Industrial Technology Research Institute, Hsinchu (TW)

(72) Inventors: Ing-Kae Wang, Hsinchu (TW); Ying-Wen Shen, Miaoli County (TW); Yea-Tzy Deng, Hsinchu (TW); Den-Tai Lin, Hsinchu (TW); Yu-Bing Liou, Hsinchu (TW); Sing-Ying Hsieh, Hsinchu (TW); Wei-Zhou Yeh, Hsinchu (TW); Meng-Hua Yang, Hsinchu (TW); Hsiang-Chun Hsu, Taipei (TW); Ying-Chun Chien, Chiayi County (TW)

(73) Assignee: Industrial Technology Research Institute, Hsinchu (TW)

( * ) Notice: Subject to any disclaimer, the term of this patent is extended or adjusted under 35 U.S.C. 154(b) by 418 days.

(21) Appl. No.: 16/226,647

(22) Filed: Dec. 20, 2018

(65) Prior Publication Data

US 2019/0203165 A1    Jul. 4, 2019

Related U.S. Application Data

(60) Provisional application No. 62/610,909, filed on Dec. 27, 2017.

(30) Foreign Application Priority Data

Dec. 14, 2018 (TW) ................... 107145323

(51) Int. Cl.
*C12M 1/26* (2006.01)
*C12M 1/40* (2006.01)
(Continued)

(52) U.S. Cl.
CPC ............ *C12M 23/04* (2013.01); *C12M 21/18* (2013.01); *C12M 23/22* (2013.01); *C12M 23/44* (2013.01);
(Continued)

(58) Field of Classification Search
None
See application file for complete search history.

(56) References Cited

U.S. PATENT DOCUMENTS 5,266,476 A    11/1993  Sussman et al.
5,686,304 A    11/1997  Codner
(Continued)

FOREIGN PATENT DOCUMENTS

CN    101541946    9/2009
CN    101748063    6/2010
(Continued)

OTHER PUBLICATIONS

Cabrita et al., Hematopoietic stem cells: from the bone to the bioreactor, Trends in Biotechnology, vol. 21 No. 5, May 2003 (Year: 2003).*
(Continued)

*Primary Examiner* — Holly Kipouros
(74) *Attorney, Agent, or Firm* — JCIPRNET

(57) ABSTRACT

A cell culture module, a cell culture system and a cell culture method are provided. The cell culture module includes a casing, a first fixer, a second fixer and a sheet-shaped carrier member. The casing has a chamber and at least one inlet/outlet. The inlet/outlet communicates with the chamber. The first fixer is fixed to the casing and located in the chamber. The second fixer is disposed in the chamber and is movable relative to the first fixer. The sheet-shaped carrier member is formed by arranging a plurality of cell culture carriers, and two opposite ends of the sheet-shaped carrier member are
(Continued)

respectively fixed to the first fixer and the second fixer. The sheet-shaped carrier member is in an open state or a folded state according to a variation in a distance between the first fixer and the second fixer due to a movement of the second fixer.

32 Claims, 19 Drawing Sheets

(51) Int. Cl.
*C12M 1/00* (2006.01)
*C12M 3/00* (2006.01)
*C12M 1/12* (2006.01)
*C12M 1/34* (2006.01)

(52) U.S. Cl.
CPC ............ *C12M 23/58* (2013.01); *C12M 25/02* (2013.01); *C12M 25/14* (2013.01); *C12M 33/00* (2013.01); *C12M 41/46* (2013.01)

(56) References Cited

U.S. PATENT DOCUMENTS

| | | | |
|---|---|---|---|
| 6,121,042 A * | 9/2000 | Peterson | C12M 41/00 435/284.1 |
| 6,245,557 B1 | 6/2001 | Fouts et al. | |
| 9,453,197 B2 | 9/2016 | Yoon et al. | |
| 2001/0043918 A1 | 11/2001 | Masini et al. | |
| 2005/0019897 A1 * | 1/2005 | Bergeron | C12M 35/04 435/284.1 |
| 2017/0166859 A1 | 6/2017 | Wang et al. | |
| 2017/0306287 A1 * | 10/2017 | Kawarai | C12M 47/02 |
| 2018/0223238 A1 | 8/2018 | Shen et al. | |
| 2020/0255784 A1 * | 8/2020 | Kaiser | C12M 23/26 |
| 2021/0222103 A1 * | 7/2021 | Martin | C12M 23/14 |

FOREIGN PATENT DOCUMENTS

| | | |
|---|---|---|
| CN | 203048948 | 7/2013 |
| JP | 2014183753 | 10/2014 |
| TW | I259203 | 8/2006 |
| TW | 201643242 | 12/2016 |
| TW | 201720915 | 6/2017 |
| WO | 2009021501 | 2/2009 |

OTHER PUBLICATIONS

"Search Report of Europe Counterpart Application", dated May 13, 2019, p. 1-p. 7.
"Office Action of Taiwan Counterpart Application," dated May 7, 2019, p. 1-p. 16.
Office Action of China Counterpart Application, dated Dec. 3, 2021, pp. 1-8.

* cited by examiner

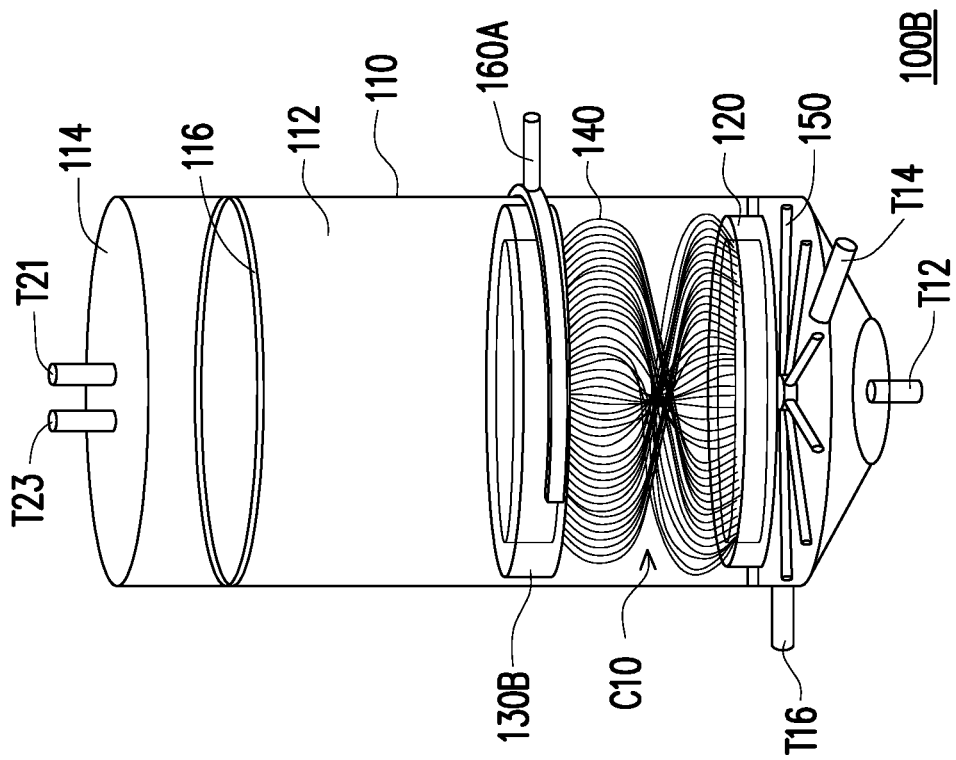
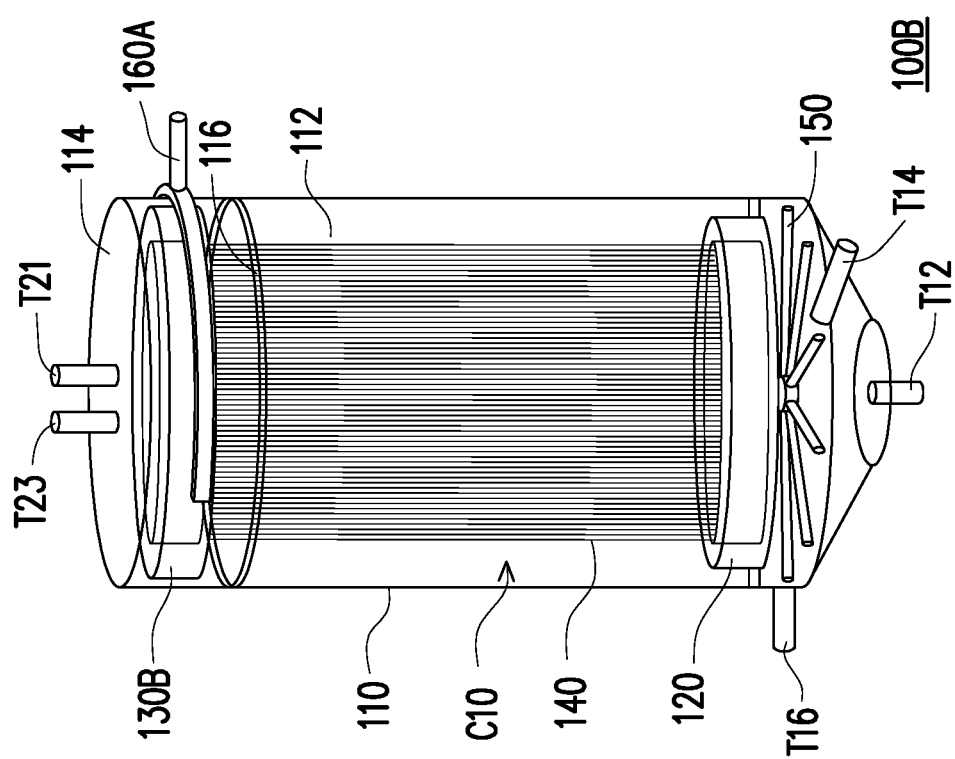

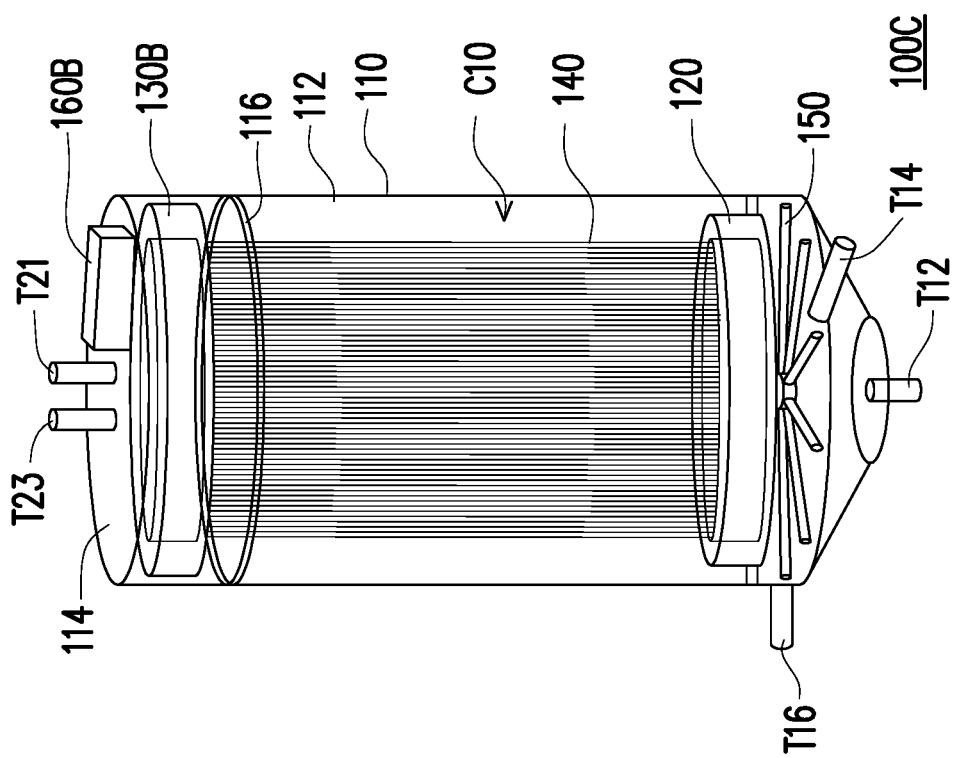

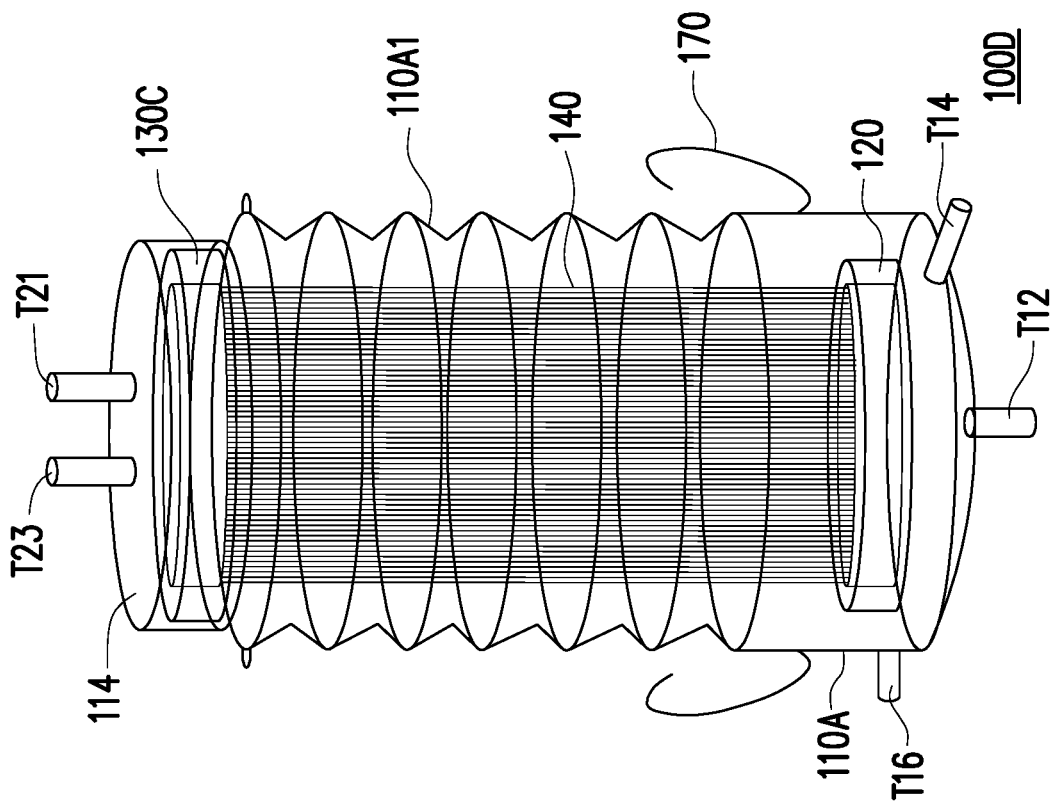
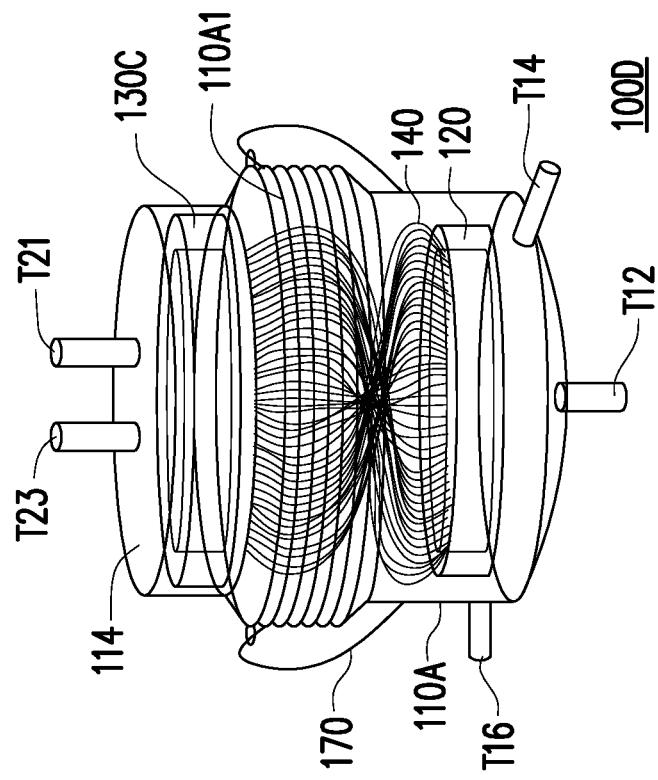
FIG. 4A
FIG. 4B

US 11,254,902 B2

CELL CULTURE MODULE, CELL CULTURE SYSTEM AND CELL CULTURE METHOD

CROSS-REFERENCE TO RELATED APPLICATION

This application claims the priority benefit of U.S. provisional application Ser. No. 62/610,909, filed on Dec. 27, 2017, and Taiwan application serial no. 107145323, field on Dec. 14, 2018. The entirety of the above-mentioned patent applications are hereby incorporated by reference herein and made a part of this specification.

TECHNICAL FIELD

The disclosure relates to a culture module, a culture system and a culture method and more particularly, to a cell culture module, a cell culture system and a cell culture method.

BACKGROUND

Current carrier scaffolds for cell mass production may be divided into two categories, one being natural materials such as collagen, chitosan, gelatin or the like and the other being synthetic materials such as polycaprolactone (PCL), polystyrene (PS), polypropylene (PP), poly(lactic-co-glycolic acid) (PLGA) or the like. The natural materials are mostly materials derived from animal sources. Although the materials derived from animal sources have lower cytotoxicity and higher biocompatibility, they may carry undetectable animal contaminants. Therefore, the current trend is toward reducing or even eliminating the use of the materials derived from animal sources to reduce the risk of contamination.

In addition, among current commercially available cell carriers, all the synthetic materials except for alginate-based related products are difficult to degrade, thus causing challenges in collecting the cells. Since the alginate-based related products require a high concentration of calcium ions during cell culture, the cells may be damaged or a tendency to differentiation may be induced in some certain cells (e.g., mesenchymal stem cells). In addition, during degradation of alginate, it is necessary to use a calcium ion chelator and improper usage thereof is very likely to cause damage to the cells. In addition, there is still room for improvement in key techniques for cell collection carrier scaffolds. Thus, current cell mass production technology still remains at a conventional two-dimensional flat plate culture method and the process cannot be adapted to larger scale production.

Therefore, to find a carrier material suitable for rapid and mass growth of cells and yet devoid of animal contaminants and to enhance cell recovery rate and cell quality are both issues that researchers are eager to solve.

SUMMARY

A cell culture module according to one or more exemplary embodiments includes a casing, a first fixer, a second fixer and a sheet-shaped carrier member. The casing has a chamber and at least one inlet/outlet. The inlet/outlet communicates with the chamber. The first fixer is fixed to the casing and located in the chamber. The second fixer is disposed in the chamber and is movable relative to the first fixer. The sheet-shaped carrier member is formed by arranging a plurality of cell culture carriers and two opposite ends of the sheet-shaped carrier member are respectively fixed to the first fixer and the second fixer. The sheet-shaped carrier member is in an open state or a folded state according to a variation in a distance between the first fixer and the second fixer due to a movement of the second fixer.

According to one or more exemplary embodiments, a cell culture system includes a cell tank, a culture medium module and a cell culture module. The cell tank and the culture medium module respectively communicate with the cell culture module and the cell culture module includes a casing, a first fixer, a second fixer and a sheet-shaped carrier member. The casing has a chamber and at least one inlet/outlet. The inlet/outlet communicates with the chamber. The first fixer is fixed to the casing and located in the chamber. The second fixer is disposed in the chamber and is movable relative to the first fixer. The sheet-shaped carrier member is formed by arranging a plurality of cell culture carriers and two opposite ends of the sheet-shaped carrier member are respectively fixed to the first fixer and the second fixer. The sheet-shaped carrier member is in an open state or a folded state according to a variation in a distance between the first fixer and the second fixer due to a movement of the second fixer.

According to one or more exemplary embodiments, a cell culture method adopts the above cell culture module and includes the following steps. Cell are attached on the sheet-shaped carrier member in the folded state. A culture medium is perfused and circulated in the cell culture module and a cell culture is started. The culture medium is discharged and a cleaning solution is perfused and then the remaining culture medium is removed by immersion and cleaning. A cell detachment enzyme is perfused. When the sheet-shaped carrier member is in the open state, the cells are desorbed from the sheet-shaped carrier member and suspended in the suspension of the cell culture module. Moreover, the suspension containing the cells is collected.

Based on the above, in the cell culture module, the cell culture system and the cell culture method according to one or more exemplary embodiments, by the second fixer, the cell culture carrier may be controlled to switch between the untwisted and twisted state or the open and folded state and cell recovery rate and cell quality may thus be enhanced.

Several exemplary embodiments accompanied with figures are described in detail below to further describe the disclosure in details.

BRIEF DESCRIPTION OF THE DRAWINGS

FIG. 2A and FIG. 2B are schematic views of a cell culture carrier of a cell culture module, in an untwisted state and a twisted state, respectively, according to another exemplary embodiment.

FIG. 3 is a schematic view of a cell culture module according to still another exemplary embodiment.

FIG. 4A and FIG. 4B are schematic views of a cell culture carrier of a cell culture module, in a twisted state and an untwisted state, respectively, according to yet still another exemplary embodiment.

DETAILED DESCRIPTION OF DISCLOSED EMBODIMENTS

Figure 1B:
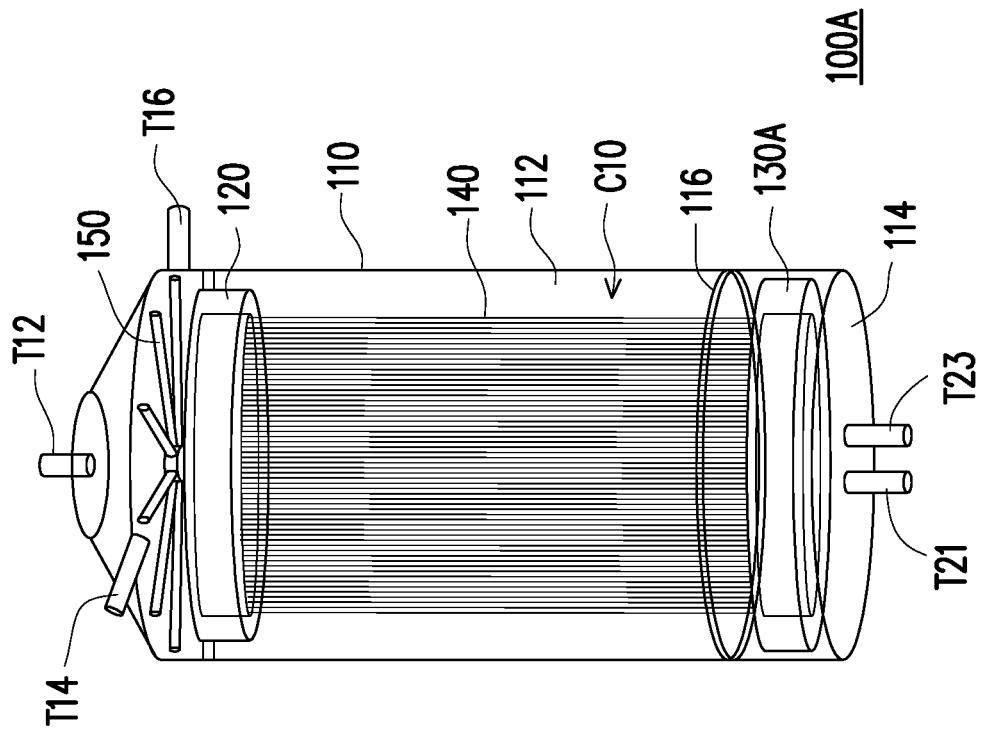
FIG. 1A and FIG. 1B are schematic views of a cell culture carrier of a cell culture module, in a twisted state and an untwisted state, respectively, according to an exemplary embodiment.

The disclosure is more comprehensively described with reference to the figures of the present embodiments. However, the disclosure may also be implemented in various different forms and is not limited to the embodiments in the present specification. The same or similar reference numerals in the figures represent the same or similar elements and are not repeated in the following paragraphs.

Figure 1A:
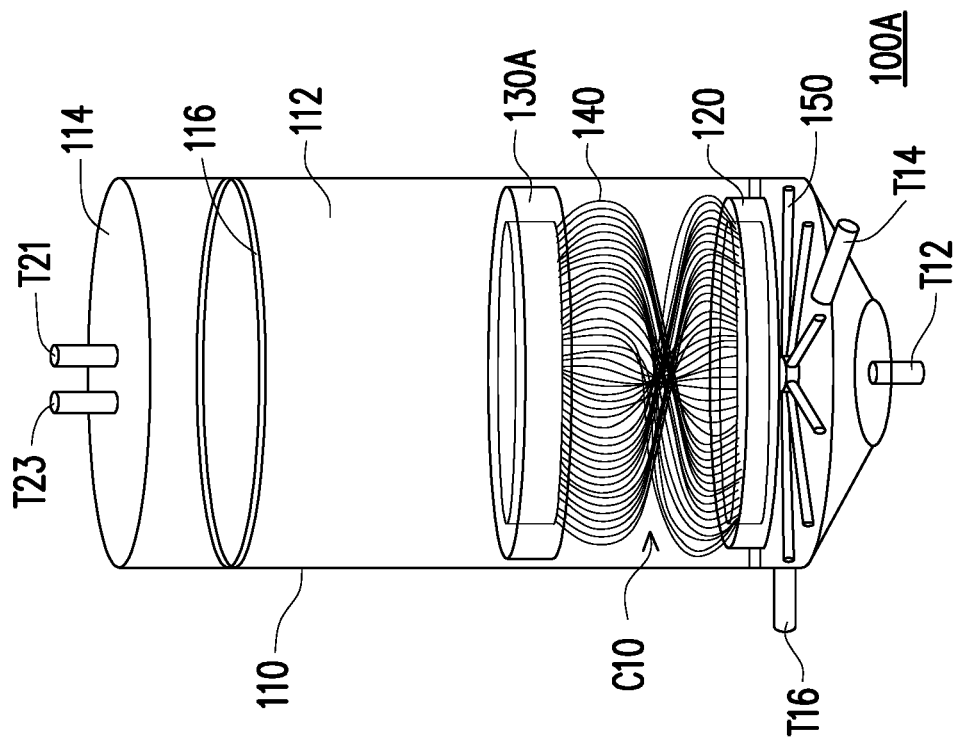

FIG. 1A and FIG. 1B are respectively schematic views of cell culture carriers of a cell culture module in a twisted state and an untwisted state according to an exemplary embodiment. Referring to FIG. 1A and FIG. 1B, a cell culture module 100A of the present embodiment includes a reactor 110, a first fixer 120, a second fixer 130A and a plurality of cell culture carriers 140. The reactor 110 has a chamber C10 and at least one inlet/outlet T12. The chamber C10 is configured to provide space for culturing cells. The inlet/outlet T12 communicates with the chamber C10. The first fixer 120 is fixed to the reactor 110 and located in the chamber C10. The second fixer 130A is disposed in the chamber C10 and is movable relative to the first fixer 120. Two ends of the cell culture carriers 140 are respectively fixed to the first fixer 120 and the second fixer 130A. The cell culture carriers 140 are in the twisted state as shown in FIG. 1A, or the cell culture carriers 140 are in the untwisted state as shown in FIG. 1B according to a variation in a distance between the first fixer 120 and the second fixer 130A due to a movement of the second fixer 130A.

In other words, when the distance between the first fixer 120 and the second fixer 130A becomes less than a stretch length of the cell culture carriers 140 due to the movement of the second fixer 130A, the cell culture carriers 140 are in the twisted state, as shown in FIG. 1A. The cell culture carriers 140 may have a strip shape. The strip-shaped cell culture carriers 140 may be used in limited space to obtain more area for cells to adhere to so as to increase the number of culturable cells.

In addition, when the distance between the first fixer 120 and the second fixer 130A becomes roughly equal to the stretch length of the cell culture carriers 140 due to the movement of the second fixer 130A, the cell culture carriers 140 are rendered in the untwisted state, as shown in FIG. 1B. In this state, the cells may be detached from the cell culture carriers 140 during a change of state of the cell culture carriers 140 from the twisted state to the untwisted state by the action of a substance such as an enzyme which may detach the cells from the cell culture carriers 140. Further, since the distance between the cell culture carriers 140 is increased, an enzyme or the like may act on cells inside the cell culture carriers 140 which are previously difficult to be acted upon by the enzyme, which conduces to enhancement of a cell recovery rate.

In the present embodiment, since the second fixer 130A is movably disposed in the chamber C10, when the reactor 110 is placed in the state of FIG. 1A, the second fixer 130A moves downward to a position close to the first fixer 120 due to its own gravity. To change the cell culture carriers 140 to the untwisted state, the reactor 110 may be placed upside down as shown in FIG. 1B and changed to a state opposite the state in FIG. 1A. In this way, the second fixer 130A moves downward to a position away from the first fixer 120 due to its own gravity, and the cell culture carriers 140 are stretched by the first fixer 120 and the second fixer 130A and changed to the untwisted state. In addition, to improve mobility of the second fixer 130A, a weight block may be installed onto the second fixer 130A to ensure that the second fixer 130A may move by its own gravity.

From another point of view, when the cell culture carriers 140 are in the untwisted state, each of the cell culture carriers 140 is equivalent to a two-dimensional structure. When the cell culture carriers 140 are in the twisted state, the interleaved cell culture carriers 140 are equivalent to a three-dimensional structure. In FIG. 1A, each of the cell culture carriers 140 in the twisted state has a regular spiral shape. However, the cell culture carrier 140 may also be randomly twisted, and thus a plurality of cell culture carriers 140 in the twisted state may have a coiling shape. However, the disclosure is not limited thereto. In FIG. 1B, each of the cell culture carriers 140 in the untwisted state has a straight strip shape, and thus a plurality of cell culture carriers 140 in the untwisted state may be arranged in an array of parallel lines. However, the cell culture carriers 140 in the untwisted state may not be parallel to one another, or some of the cell culture carriers 140 may be slightly bent. However, the disclosure is not limited thereto.

A material of the cell culture carriers 140 includes, for example, polyester (PET), nylon, polyethylene (PE), polypropylene (PP), polyvinyl chloride (PVC), polystyrene (PS), polycarbonate (PC), ethylene vinyl acetate (EVA), polyurethane (PU) or the like. However, the disclosure is not limited thereto, and any material having fiber drawing properties may be used as the material for the cell culture carrier of the disclosure. In addition, each of the cell culture carriers 140 may be in the shape of a striped sheet, a threadlike sheet, or in any other suitable shape.

The cell culture carriers 140 may be a material to which cells may adhere or a material having cell adhesion properties after processing. The above processing methods include surface modification, surface coating, surface microstructurization or the like. Surface modification is achieved by, for example, performing plasma modification on a surface of the material to which cells may adhere, or a surface of a material to which cells cannot adhere to impart the cell adhesion properties to the surface, thereby facilitating adhesion of the cells. Surface coating includes coating, for example but not limited to, collagen, chitosan, gelatin, alginate or the like, onto the surface of the material to which cells may adhere or the surface of the material to which cells cannot adhere, thereby facilitating adhesion of the cells. Surface microstructurization is achieved by, for example, performing laser cutting on the surface of the material to which cells may adhere or the surface of the material to which cells cannot adhere so as to form microchannels, thereby facilitating adhesion of the cells. However, the cell processing methods of the disclosure are not limited thereto, and any processing method capable of enhancing cell adhesion properties may be applied in the disclosure.

A material of the reactor 110, the first fixer 120 and the second fixer 130A includes, for example, polyester (PET), nylon, polyethylene (PE), polypropylene (PP), polyvinyl chloride (PVC), polystyrene (PS), ethylene vinyl acetate (EVA), polyurethane (PU), polycarbonate (PC), glass or the like. However, the disclosure is not limited thereto.

In one exemplary embodiment, the inlet/outlet T12 of the cell culture module 100A may be disposed on one end portion of the reactor 110. When only one single inlet/outlet T12 is disposed in the cell culture module 100A, the inlet/outlet T12 may be used both for entry and exit of a liquid such as a culture medium and a buffer solution and for cell collection. However, in other exemplary embodiments, the entry and exit of the culture medium and the buffer solution and the cell collection may respectively use different channels, in view of preventing the whole module from contamination. In detail, the cell culture module 100A of the present embodiment may include a plurality of inlets/outlets T12, T14, T16, T18 (not illustrated), T21 and T23, wherein the inlet/outlet T12 is disposed on one end portion of the reactor 110 and enables the cell collection. The inlets/outlets T14, T16 and T18 may be disposed on a side surface of the reactor 110 and close to the end portion of the reactor 110 on which the inlet/outlet T12 is disposed, so as to allow entry of different buffer solutions and culture media into the reactor 110. It should be noted that the numbers of the inlets/outlets T14, T16 and T18 may vary depending on the type and requirements of the actually injected liquid, and are not limited to those mentioned herein. The inlets/outlets T21 and T23 are disposed on the other end portion of the reactor 110, opposite the inlet/outlet T12. The inlet/outlet T21 allows the entry and exit of liquid such as a culture medium or a buffer solution, and the inlet/outlet T23 is a reserved hole, wherein the design in which the inlet/outlet T21 is located opposite the inlets/outlets T14, T16 and T18 facilitates distribution and circulation of liquid within the chamber C10.

The cell culture module 100A of the present embodiment may further include a turbulent part 150 disposed in the chamber C10 and between the inlet/outlet T12 and the first fixer 120. To be specific, the turbulent part 150 may be arranged at the same plane height as the inlets/outlets T14, T16 and T18. The liquid that enters via the inlets/outlets T14, T16 and T18, after being rotated by the turbulent part 150, may drive circulation of the liquid in the chamber C10. As a result, substances in the liquid in the chamber C10 may be uniformly distributed.

The cell culture module may have different designs depending on whether it is reusable. When the cell culture module is reusable, as shown in the present embodiment, the reactor 110 of the cell culture module 100A further includes a body 112 and a cover 114, the body 112 and the cover 114 being connected with each other to form the chamber C10. By opening the cover 114, the communication with the chamber C10 becomes possible so that the cell culture carriers 140 may be replaced. In addition, a sealing part 116 may further be disposed between the body 112 and the cover 114 to maintain sealability of the chamber C10. When the cell culture module is for one time use only, the reactor 110 is integrally formed.

FIG. 2A and FIG. 2B are schematic views of a cell culture carrier of a cell culture module, in the untwisted state and the twisted state, respectively, according to another exemplary embodiment. Referring to FIG. 2A and FIG. 2B, a cell culture module 100B of the present embodiment is similar to the cell culture module 100A of FIG. 1A. Nonetheless, it should be noted that the cell culture module 100B of the present embodiment further includes a magnetic control part 160A. Correspondingly, a second fixer 130B of the present embodiment has magnetism. Accordingly, the magnetic control part 160A may control the second fixer 130B to move, using magnetic force such as magnetic attractive force or magnetic repulsive force. As shown in FIG. 2A, when the magnetic control part 160A magnetically controls the second fixer 130B to move to a position away from the first fixer 120, the cell culture carriers 140 are rendered in the untwisted state. As shown in FIG. 2B, when the magnetic control part 160A controls the second fixer 130B to move to a position close to the first fixer 120, the cell culture carriers 140 are rendered in the twisted state. The shape of the magnetic control part 160A of the present embodiment roughly matches the shape of the reactor 110. Moreover, the magnetic control part 160A itself is movable, thereby driving the second fixer 130B to move. However, the disclosure is not limited thereto.

FIG. 3 is a schematic view of a cell culture module according to still another exemplary embodiment. Referring to FIG. 3, a cell culture module 100C of the present embodiment is similar to the cell culture module 100B of FIG. 2A. Nonetheless, it should be noted that, when a magnetic control part 160B of the present embodiment intends to control the second fixer 130B to move, the magnetic control part 160B directly moves to one side of the reactor 110 away from the first fixer 120 and then uses magnetic force to attract the second fixer 130B to move to a position away from the first fixer 120. By contrast, after the magnetic control part 160B is removed, the second fixer 130B will move to a position close to the first fixer 120 due to its own gravity.

FIG. 4A and FIG. 4B are schematic views of a cell culture carrier of a cell culture module, in the twisted state and the untwisted state, respectively, according to yet still another exemplary embodiment. Referring to FIG. 4A and FIG. 4B, a cell culture module 100D of the present embodiment is similar to the cell culture module 100A of FIG. 1A. Nonetheless, it should be noted that the cell culture module 100D of the present embodiment further includes a fastener 170. In addition, a reactor 110A further includes an elastic corrugated structure 110A1. When no force is applied thereto, the elastic corrugated structure 110A1 is, for example, in a stretched state as shown in FIG. 4B. The fastener 170 is configured to control the elastic corrugated structure 110A1 to remain in a compressed state or not, so that the elastic corrugated structure 110A1 may switch between the stretched state as shown in FIG. 4B and the compressed state as shown in FIG. 4A. A second fixer 130C of the present embodiment is fixed to the reactor 110A, and the elastic corrugated structure 110A1 is located between the first fixer 120 and the second fixer 130C. When the fastener 170 is fastened, the elastic corrugated structure 110A1 is in the compressed state. Thus, the first fixer 120 and the second fixer 130C approach each other to render the cell culture carriers 140 in the twisted state. When the fastener 170 is released, the elastic corrugated structure 110A1 is in the stretched state. Thus, the first fixer 120 and the second fixer 130C are away from each other to render the cell culture carriers 140 in the untwisted state. It should be noted that although the fastener 170 is taken as an example in the present embodiment, the fastener 170 may also be arbitrarily replaced with other fixers, such as a velcro, a screw, a rope and the like.

Figure 5:
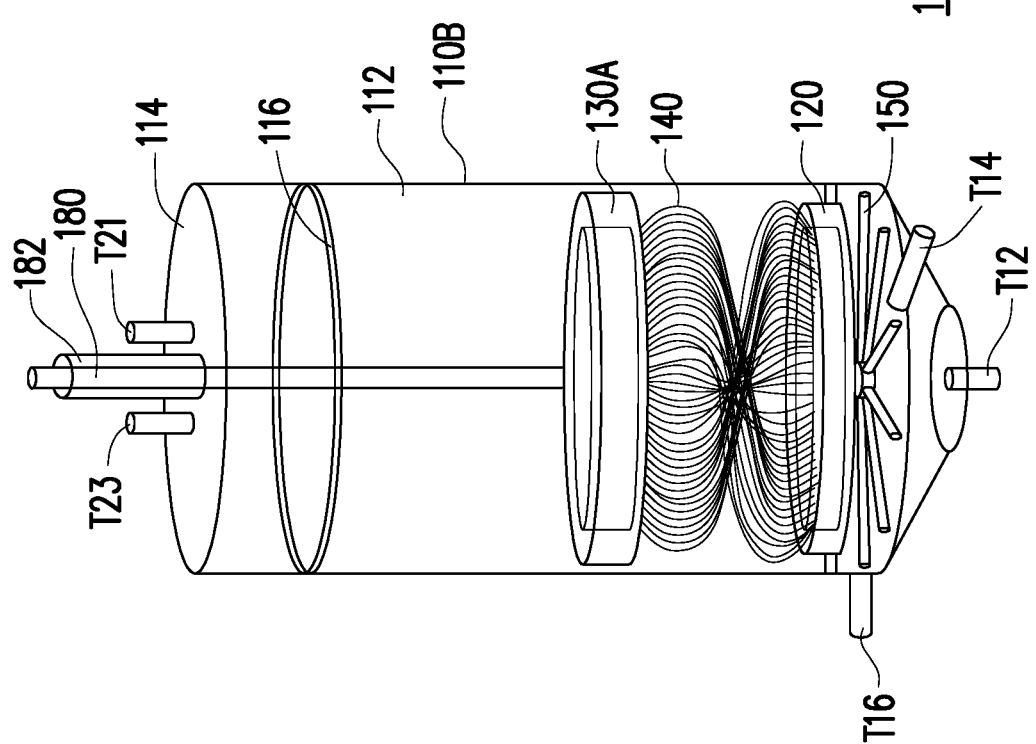
FIG. 5 is a schematic view of a cell culture module according to further still another exemplary embodiment.

FIG. 5 is a schematic view of a cell culture module according to further still another exemplary embodiment. Referring to FIG. 5, a cell culture module 100E of the present embodiment is similar to the cell culture module 100A of FIG. 1A. Nonetheless, it should be noted that the cell culture module 100E of the present embodiment further includes a rod 180 and a guide hole 182. The guide hole 182 is disposed on one end of a reactor 110B, opposite the first fixer 120, so as to guide the rod 180 to be movably inserted through the reactor 110B. The rod 180 is connected to the second fixer 130A and configured to control the second fixer 130A to move. By controlling the extent to which the rod 180 is inserted into the reactor 110B, it is possible to control the second fixer 130A to move to a position close to or away from the first fixer 120.

Figure 6:
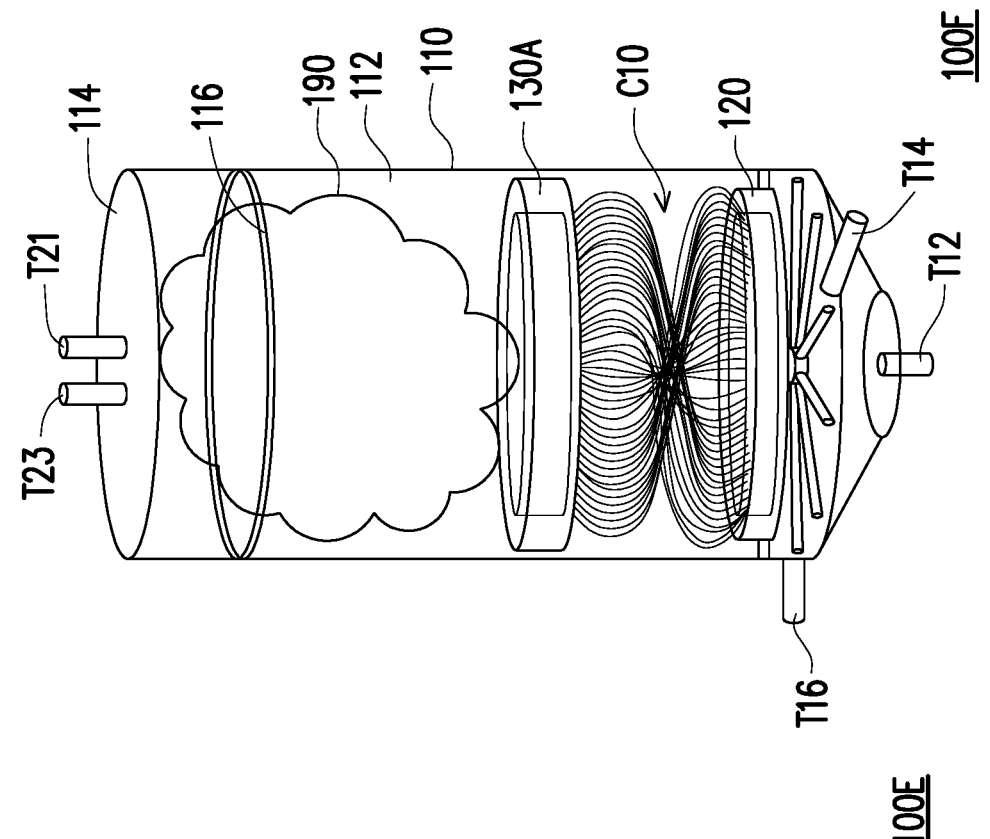
FIG. 6 is a schematic view of a cell culture module according to another exemplary embodiment.

FIG. 6 is a schematic view of a cell culture module according to another exemplary embodiment. Referring to FIG. 6, a cell culture module 100F of the present embodiment is similar to the cell culture module 100A of FIG. 1A. Nonetheless, it should be noted that the cell culture module 100F of the present embodiment further includes a fluid pressure control part 190 disposed in the reactor 110 and inside the chamber C10. The second fixer 130A is located between the fluid pressure control part 190 and the first fixer 120. The fluid pressure control part 190 is configured to control the second fixer 130A to move. For example, the fluid pressure control part 190 is applicable to bags for containing fluids. However, the disclosure is not limited thereto. As a gas, water, oil or other fluid contained in the fluid pressure control part 190 increases, the volume of the fluid pressure control part 190 also increases, thus pushing the second fixer 130A to move in a direction approaching the first fixer 120. As the gas, water, oil or other fluid contained in the fluid pressure control part 190 decreases, the volume of the fluid pressure control part 190 also decreases, thus allowing the second fixer 130A to move in a direction away from the first fixer 120.

Figure 7:
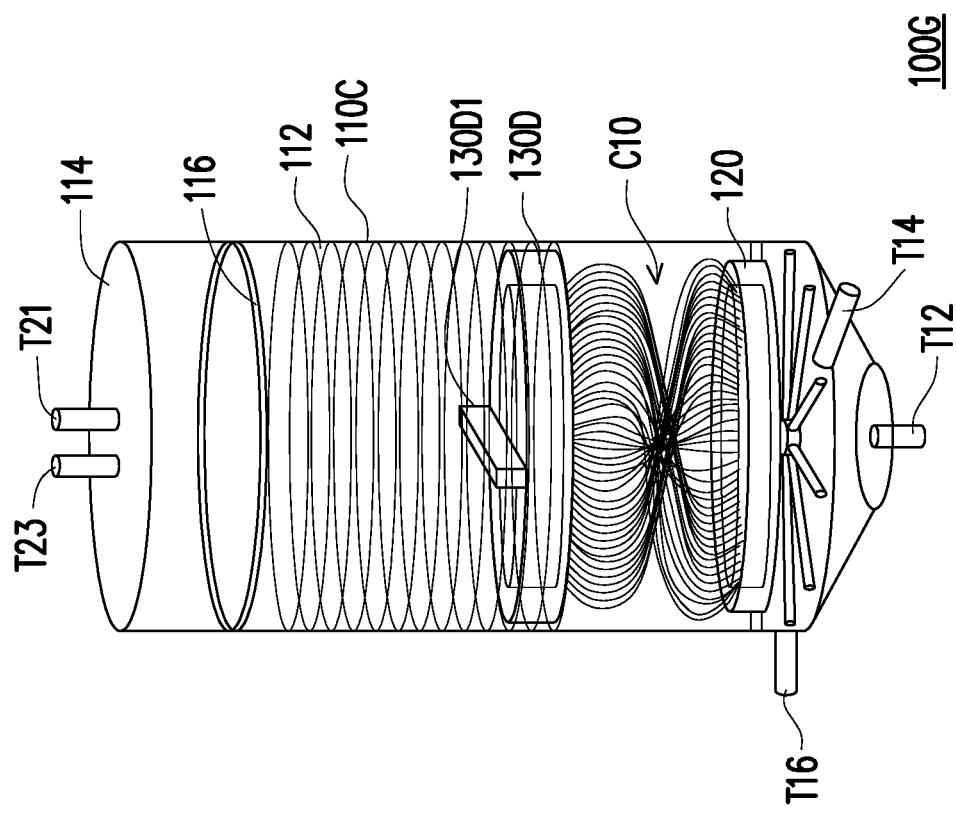
FIG. 7 is a schematic view of a cell culture module according to still another exemplary embodiment.

FIG. 7 is a schematic view of a cell culture module according to still another exemplary embodiment. Referring to FIG. 7, a cell culture module 100G of the present embodiment is similar to the cell culture module 100A of FIG. 1A. Nonetheless, it should be noted that, in the cell culture module 100G of the present embodiment, a second fixer 130D is screwed onto a wall of a reactor 110C. In other words, screw threads matching each other are provided on contact surfaces of both the second fixer 130D and the reactor 110C. Accordingly, when the second fixer 130D is rotated relative to the reactor 110C, the second fixer 130D approaches or departs from the first fixer 120. A knob 130D1 is further provided on the second fixer 130D of the present embodiment to enable a user to easily apply force to rotate the second fixer 130D.

Figure 8A:
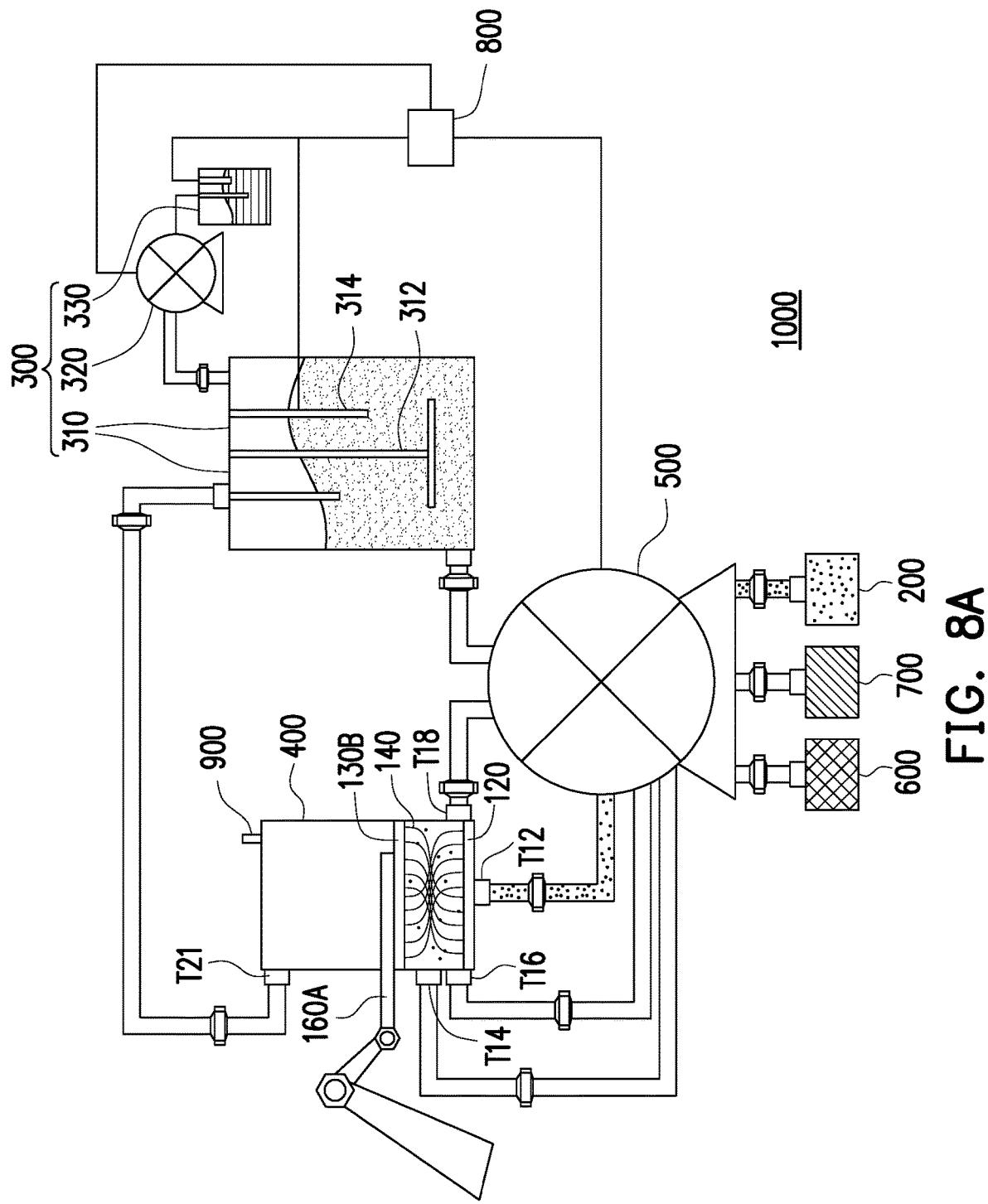
FIG. 8A to FIG. 8F are schematic views illustrating several stages of a cell culture performed by a cell culture system according to an exemplary embodiment.

FIG. 8A to FIG. 8F are schematic views illustrating several stages of a cell culture performed by a cell culture system according to an exemplary embodiment. Referring first to FIG. 8A, a cell culture system 1000 of the present embodiment includes a cell tank 200, a culture medium module 300 and a cell culture module 400. The cell tank 200 and the culture medium module 300 respectively communicate with the cell culture module 400. The cell culture module 400 may be any cell culture module of the aforesaid embodiments or any other cell culture module complying with the spirit of the disclosure. The details of the cell culture module 400 are omitted herein. Since the cell culture system 1000 of the present embodiment uses the cell culture module 400 that is the same as the cell culture module of the aforesaid embodiments, the cell culture system 1000 of the present embodiment may enhance the yield and the recovery rate of cell culture. In addition, the cell culture system 1000 of the present embodiment may optionally further include a pump 500, a cleaning solution tank 600 and a cell detachment enzyme tank 700. The cell tank 200 and the culture medium module 300 respectively communicate with the cell culture module 400 via the pump 500. Both the cleaning solution tank 600 and the cell detachment enzyme tank 700 also communicate with the cell culture module 400 via, for example, the pump 500.

In the present embodiment, the cell tank 200, the culture medium module 300, the cleaning solution tank 600 and the cell detachment enzyme tank 700 all communicate with the cell culture module 400 via the pump 500. The cell tank 200 is connected to the pump 500 by which the cell tank 200 is connected to the inlet/outlet T12 of the cell culture module 400. The cleaning solution tank 600 is connected to the pump 500 by which the cleaning solution tank 600 is connected to the inlet/outlet T14 of the cell culture module 400. The cell detachment enzyme tank 700 is connected to the pump 500 by which the cell detachment enzyme tank 700 is connected to the inlet/outlet T16 of the cell culture module 400. The culture medium module 300 is connected to the pump 500 by which the culture medium module 300 is connected to the inlet/outlet T18 of the cell culture module 400. The culture medium of the culture medium module 300 enters the cell culture module 400 via the inlet/outlet T18, and then flows back from the cell culture module 400 to the culture medium module 300 via the inlet/outlet T21 on the other end. Therefore, the culture medium of the culture medium module 300 may be recycled for use. To monitor quality of the culture medium of the culture medium module 300, a culture medium tank 310 of the culture medium module 300 is equipped with a culture medium sensor 314. The culture medium sensor 314 is, for example, a pH meter, a thermometer, or a dissolved oxygen meter. In addition, a stirring bar 312 is further disposed in the culture medium tank 310 to maintain uniform distribution of culture substances in the culture medium. In addition, the culture medium module 300 is further equipped with a pump 320 and a regulator 330. When the culture medium sensor 314 senses that the quality of the culture medium in the culture medium tank 310 is lower than a threshold value, the pump 320 extracts regulating substances from the regulator 330 into the culture medium tank 310 so as to improve the quality of the culture medium. A cell culture system 1000 of the present embodiment may further include a controller 800. The controller 800 is connected to the cell tank 200, the cleaning solution tank 600, the cell detachment enzyme tank 700, the cell culture module 400 and the culture medium module 300 respectively via the pump 500, the culture medium sensor 314 and the pump 320 to control the pump 500, the pump 320, the regulator 330 and the culture medium sensor 314. In addition, the cell culture system 1000 of the present embodiment may further include a regulator 900 installed onto the cell culture module 400, for regulating the substances in the cell culture module 400 when necessary.

Figure 9:
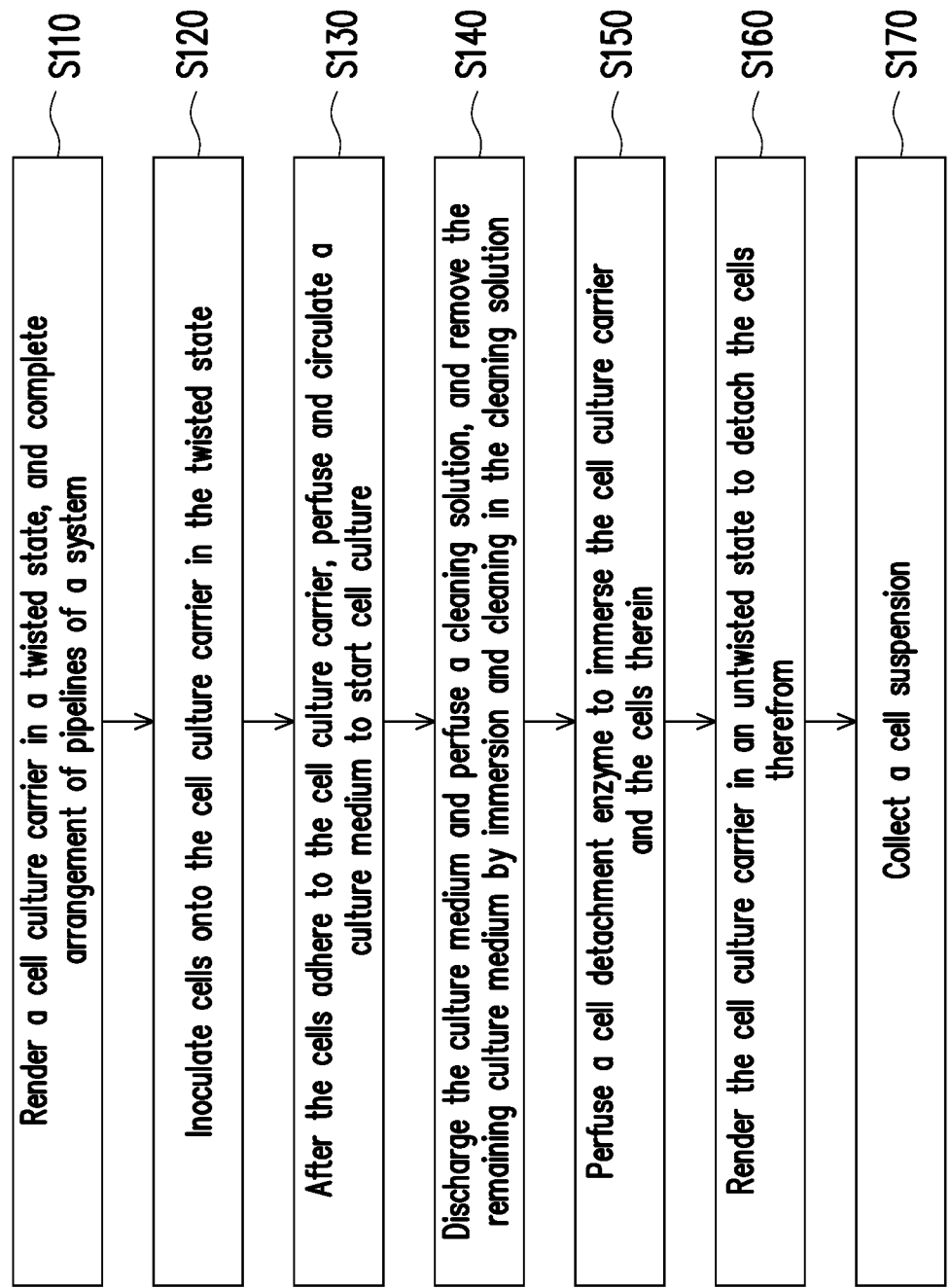
FIG. 9 is a flowchart of a cell culture method that may be performed by a cell culture system and a cell culture module according to an exemplary embodiment.

FIG. 9 is a flowchart of a cell culture method that may be performed by a cell culture system and a cell culture module according to an exemplary embodiment. Referring to FIG. 8A and FIG. 9, during a cell culture process, first of all, the cell culture carrier 140 of the cell culture module 400 is rendered in the twisted state, and arrangement of pipelines of the system is completed (step S110). As mentioned in the aforesaid embodiments, a method of rendering the cell culture carrier 140 of the cell culture module 400 in the twisted state includes causing the second fixer 130A to move to a position close to the first fixer 120. However, the way of performing the method is not limited. As in the aforesaid embodiments, the second fixer 130A may be displaced through gravity, magnetic force, or other mechanical force. In the present embodiment, the movement of the second fixer 130A may be controlled with the assistance of the magnetic control part 160A, but is not limited thereto.

Referring to FIG. 8A and FIG. 9, next, cells in the cell tank 200 which are to be cultured are sent to the cell culture module 400 using the pump 500, so as to inoculate the cells to be cultured onto the cell culture carrier 140 in the twisted state (step S120). The cells to be cultured are, for example but not limited to, stem cells or differentiated cells. Specifically, the cells to be cultured are, for example but not limited to, African green monkey kidney cell line (Vero), human adipose-derived stem cells (ADSCs), mesenchymal stem cells (MSCs), Madin-Darby Canine Kidney (MDCK) cells, human embryonic kidney cells 293 (HEK 293 cells) or the like. In the present embodiment, a culture medium is first added to the cell culture carrier 140, and the cells are then inoculated to the cell culture carrier 140. In another exemplary embodiment, a cell culture medium containing the cells may be uniformly added directly to the cell culture carrier 140. The culture medium is a standard growth culture medium commonly used for cell culture, and examples thereof include a culture medium having fetal bovine serum (FBS) or a serum-free medium. However, the disclosure is not limited thereto. In addition, it should be understood that, depending on different cell properties, requirements of operating concentration of the cell culture medium is different. Hence, the operating concentration may be adjusted according to cell properties, and growth factors, antibiotics or the like may be added to the culture medium if needed. The cells are caused to adhere to the cell culture carrier. In the present embodiment, the cell culture carrier 140 is placed in the cell culture module 400 under specific growth conditions (e.g., specific temperature, humidity, or carbon dioxide concentration) such that the cells adhere to the cell culture carrier 140.

In other exemplary embodiments, each pipeline of the system may also be configured first when the cell culture carriers 140 are in the untwisted state and then the cell culture carriers 140 in the untwisted state are inoculated. When the cells are attached, the twisting action of the cell culture carriers 140 is performed, but the disclosure is not limited to the above.

Figure 8B:
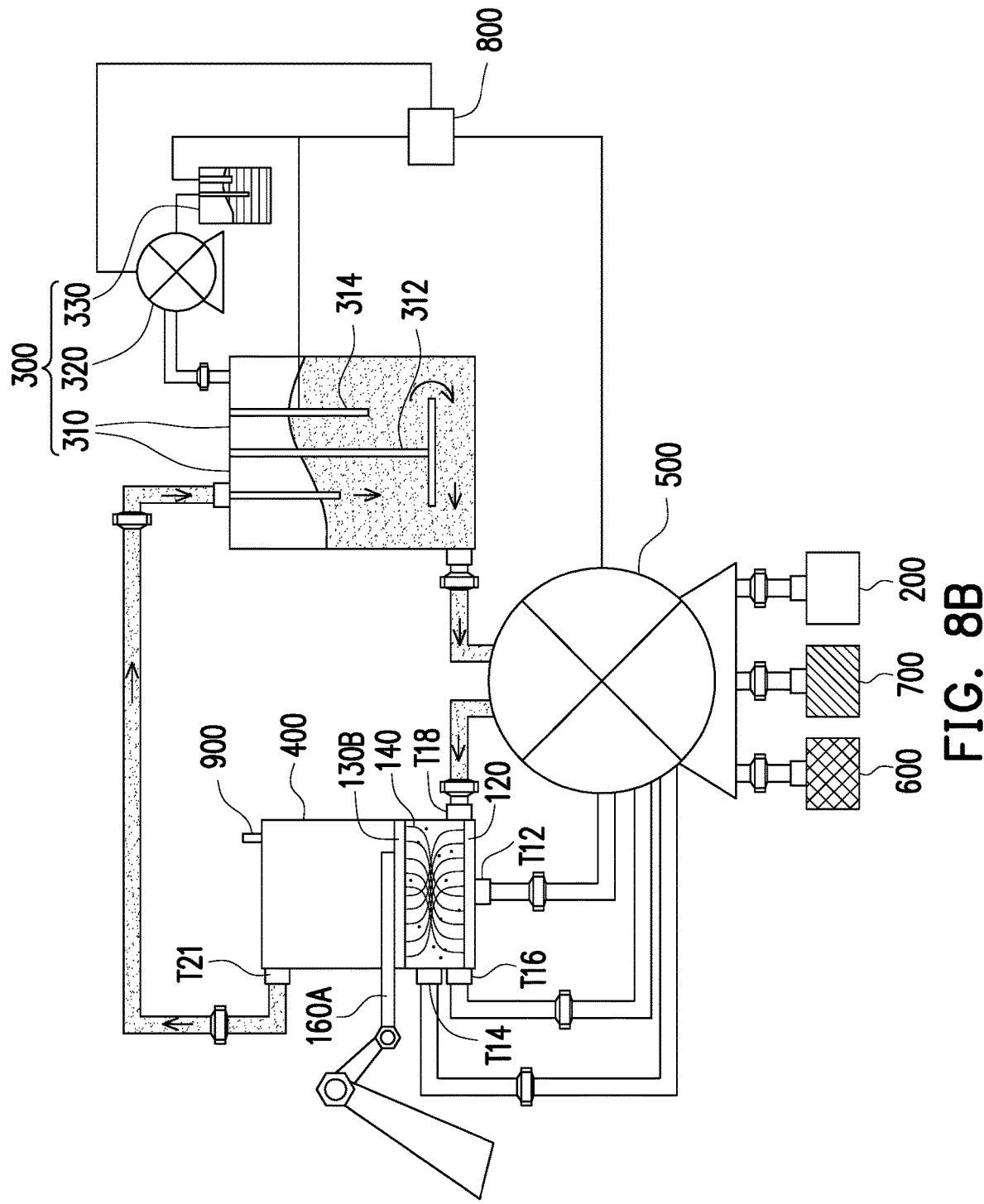

Referring to FIG. 8B and FIG. 9, next, after the cell adhesion, a culture medium is perfused and circulated to start the cell culture (step S130). That is, after the aforesaid steps are completed, the pump 500 may be turned on to allow the culture medium of the culture medium module 300 to flow into the cell culture module 400, and the culture medium is continuously circulated between the culture medium module 300 and the cell culture module 400 so as to culture the cells. The cell culture is performed by, for example, static culture or dynamic culture. The dynamic culture may be performed by disturbing the culture medium surrounding the cell culture carrier. A method of disturbing the culture medium includes, for example, using the turbulent part 150 as in FIG. 1A, which is but not illustrated in the present embodiment. In one exemplary embodiment, the number of cells after culture may increase to 100 times or more the original number of cells. In another exemplary embodiment, the number of cells after culture may increase to 2000 times or more the original number of cells.

It is noting that since different cells have different properties, the cell culture conditions may be adjusted based on different cell types. For example, when culturing mammalian cells, the cells may be cultured at conditions of 37° C. and 5% of $CO_2$, and the pH value of the culture medium is maintained within a physiological range thereof. For example, for most animal cells, a suitable pH value of the culture medium is 7.2 to 7.4.

Figure 8C:
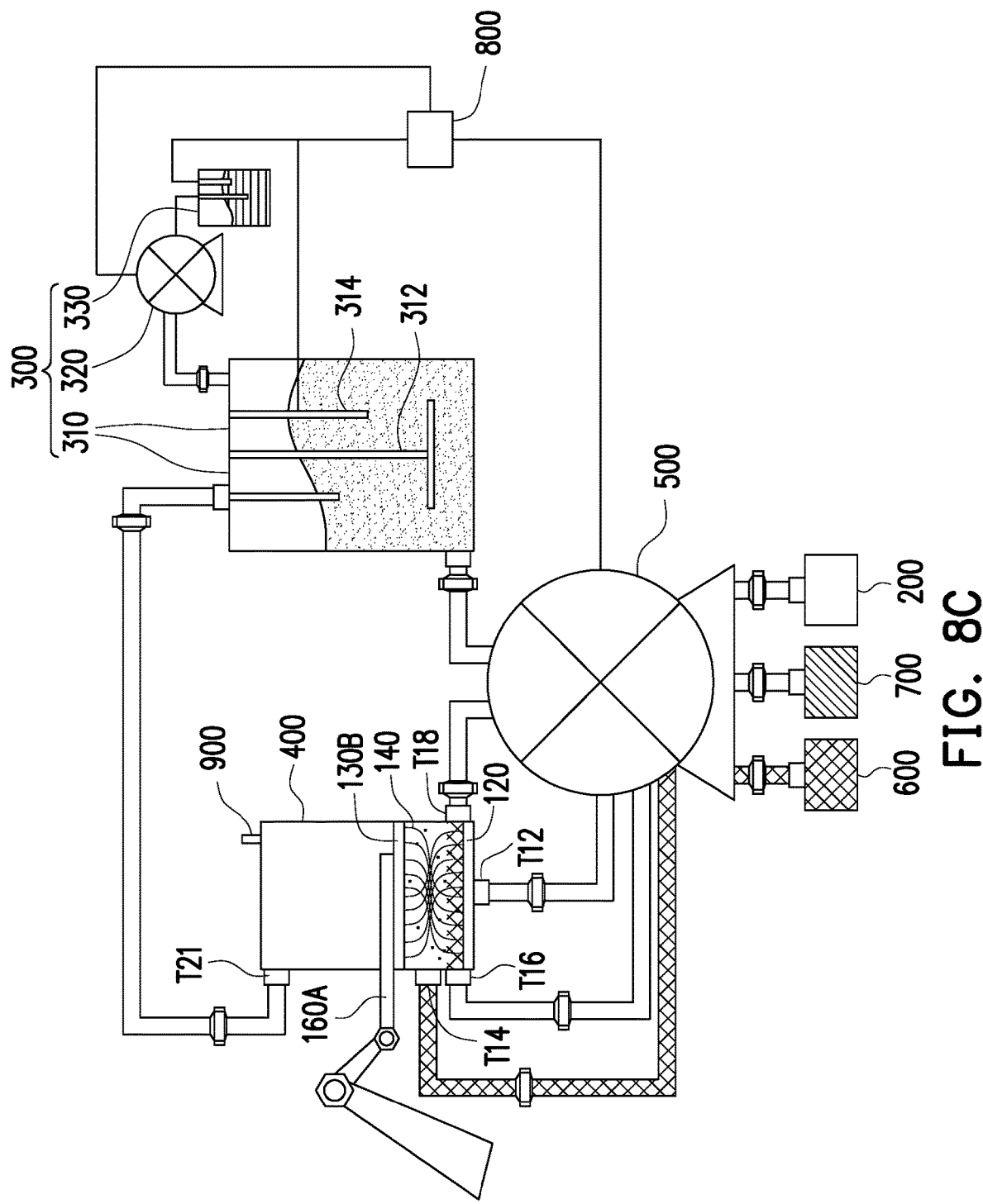

Referring to FIG. 8C and FIG. 9, next, the culture medium is discharged and a cleaning solution is perfused, and the remaining culture medium is removed by immersion and cleaning in the cleaning solution (step S140). That is, all of the culture medium in the cell culture module 400 is sent back to the culture medium module 300. Then, the cleaning solution in the cleaning solution tank 600 is caused to flow into the cell culture module 400 by the pump 500, and the remaining culture medium is removed by immersion and cleaning in the cleaning solution. The cleaning solution is, for example, a phosphate buffered saline solution.

Figure 8D:
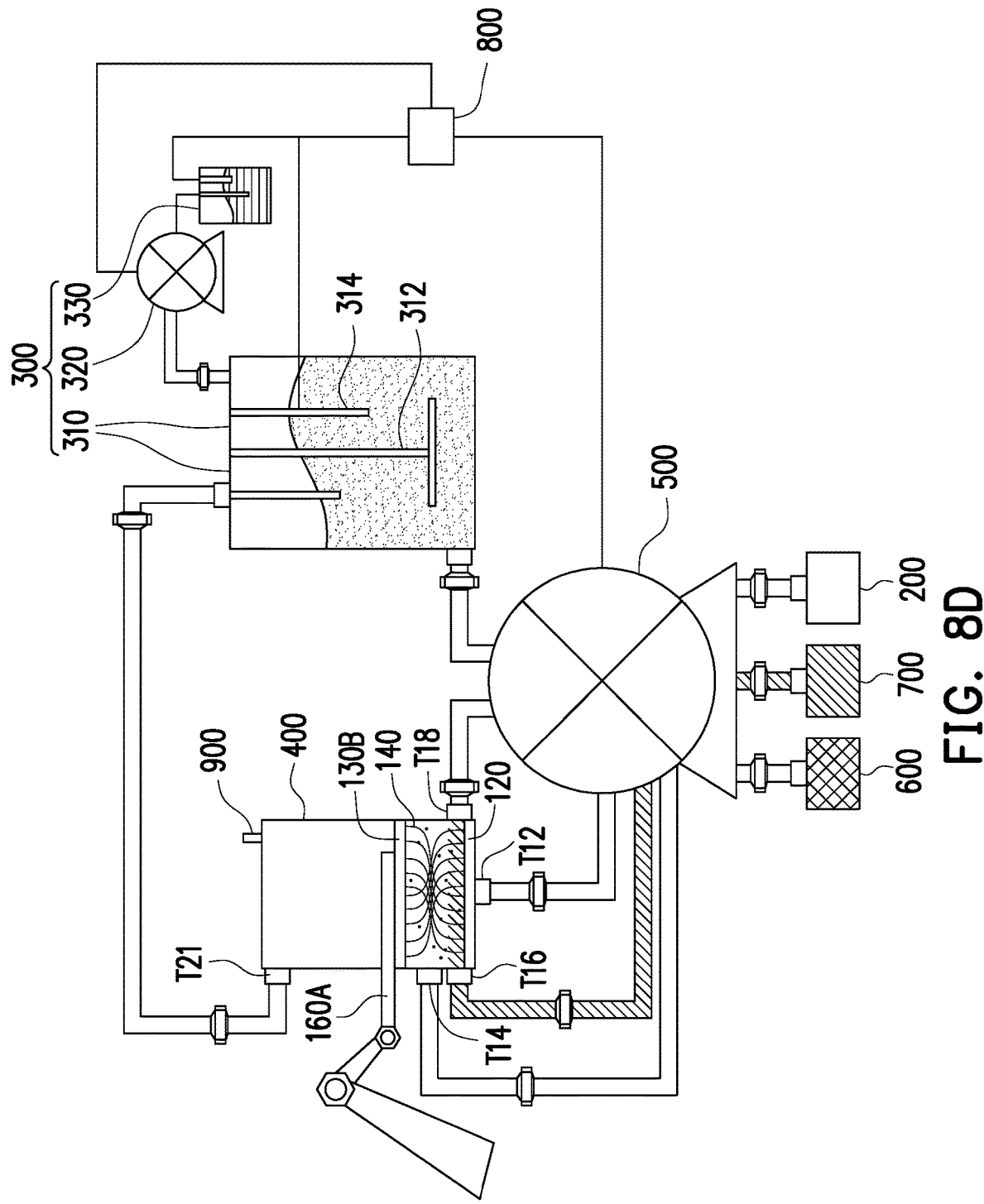

Referring to FIG. 8D and FIG. 9, next, a cell detachment enzyme is perfused to immerse the cell culture carrier and the cells therein (step S150). That is, all of the cleaning solution in the cell culture module 400 is sent back to the cleaning solution tank 600. Then, the cell detachment enzyme in the cell detachment enzyme tank 700 is caused to flow into the cell culture module 400 by the pump 500, and the cell culture carrier 140 in the twisted state and the cells are immersed in the cell detachment enzyme. The cell detachment enzyme is, for example, trypsin, tryp LE, accutase, accumax, or collagenase. However, the disclosure is not limited thereto, and other enzymes or reagents capable of cell detachment may also be used.

Figure 8E:
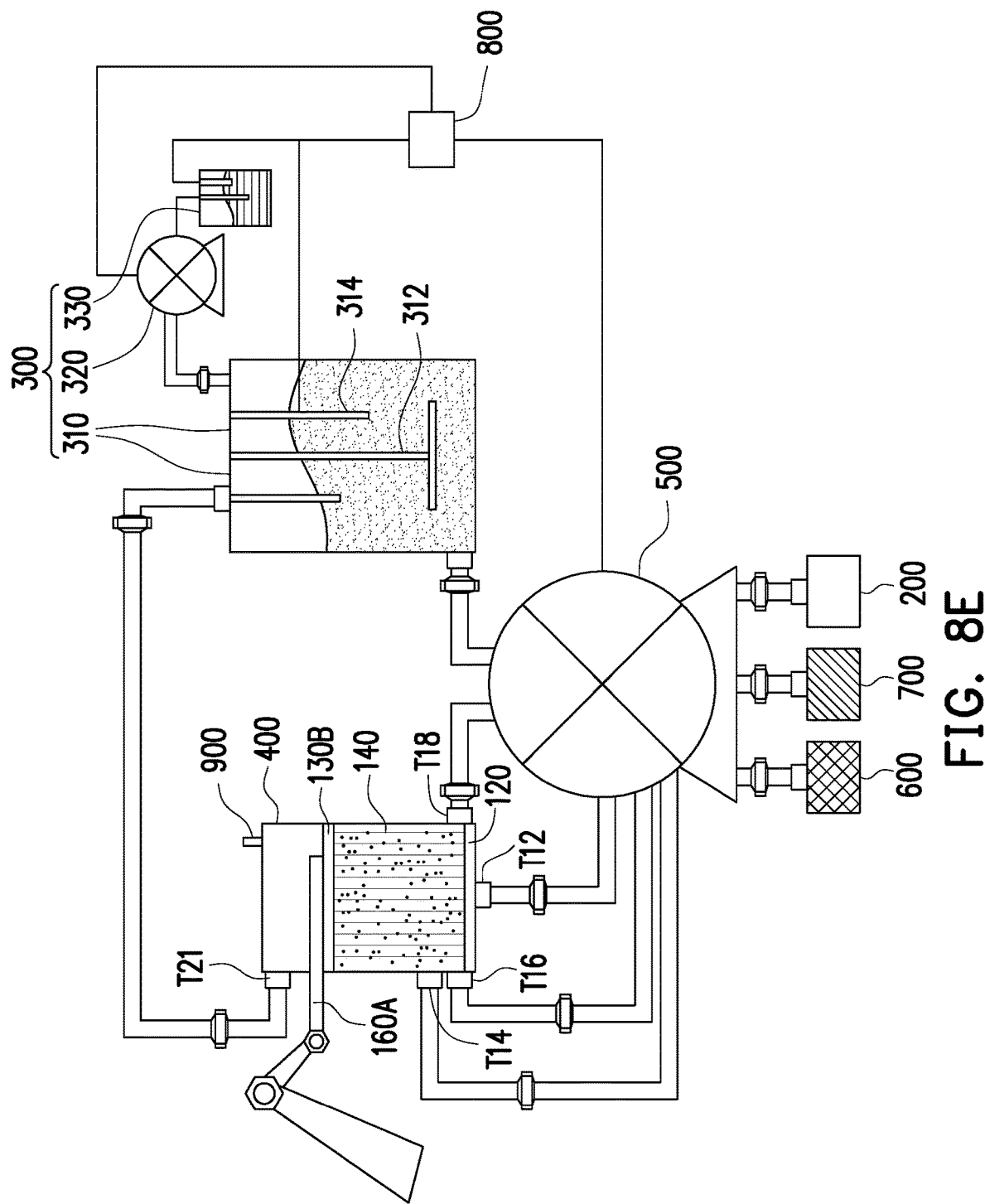

Referring to FIG. 8E and FIG. 9, next, the cell culture carrier is loosened and transformed into a two-dimensional structure, causing detachment of the cells (step S160). That is, the cell culture carrier 140 of the cell culture module 400 is changed from the twisted state to the untwisted state. As mentioned in the aforesaid embodiments, a method of rendering the cell culture carrier 140 of the cell culture module 400 in the untwisted state includes causing the second fixer 130A to move to a position away from the first fixer 120. In the present embodiment, the movement may be performed with the assistance of the magnetic control part 160A.

Figure 8F:
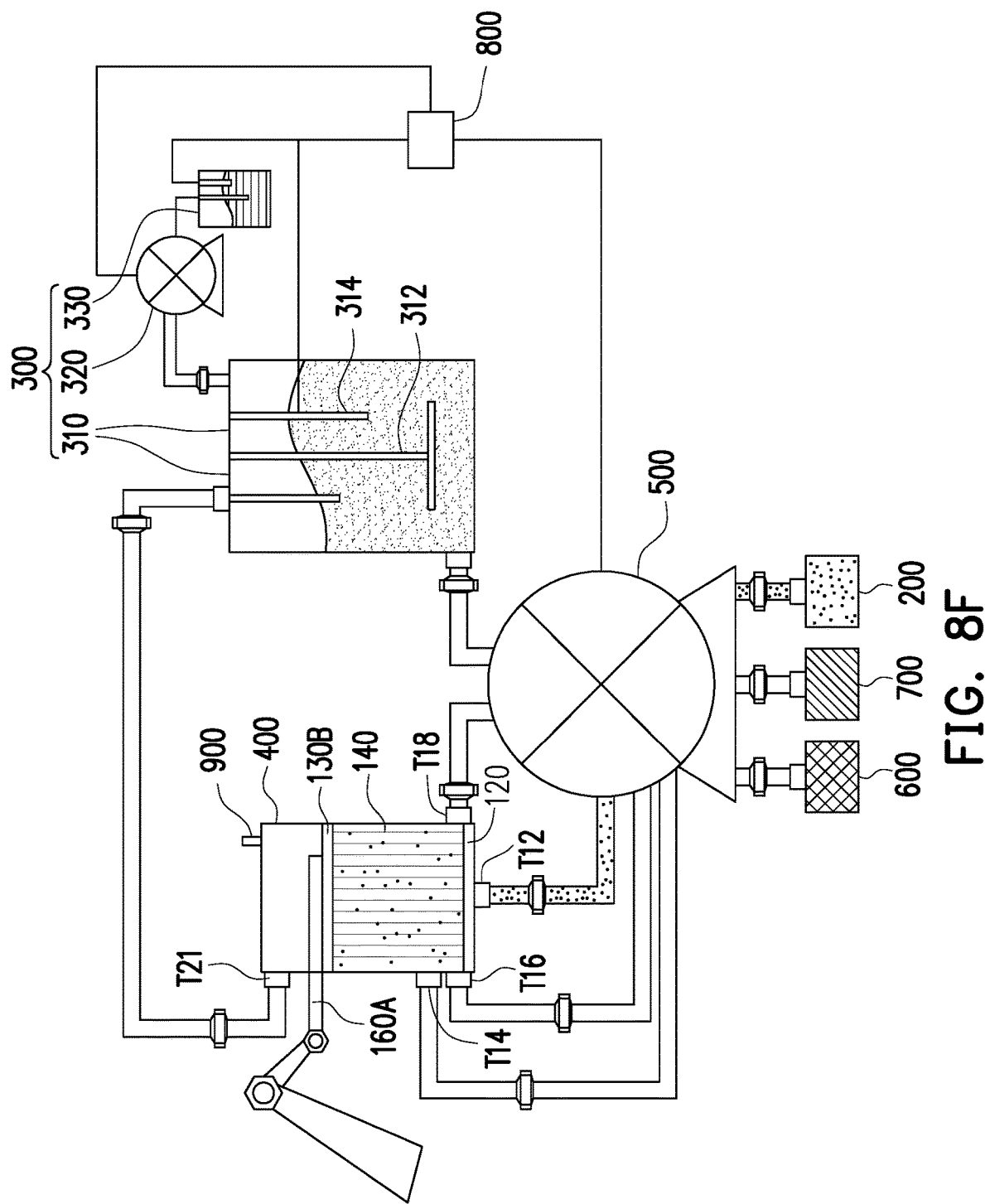

Referring to FIG. 8F and FIG. 9, next, a cell suspension is collected (step S170). That is, a cell suspension in the cell culture module 400 is sent to the cell tank 200 through the pump 500. Since the cell recovery is performed when the cell culture carrier 140 is in the untwisted state, the loosened structure allows the cell culture carrier 140 to sufficiently react with a reagent containing the cell detachment enzyme, and the loosened structure also facilitates the detachment of the cells on an inner layer of the cell culture carrier 140, thereby enhancing the cell recovery rate.

It should be noted that, in the aforesaid embodiments, the cell culture carrier 140 is loosened after the cell detachment enzyme is perfused, and the cells are then collected. However, in other exemplary embodiments, the cell culture carrier 140 may first be loosened to return to the two-dimensional state. The cell detachment enzyme is then perfused to collect the cultured cells. The disclosure is not limited to the above description.

In the above embodiments, the reactor of the cell culture module is cylindrical, but is not limited thereto. In other exemplary embodiments, the cell culture module may also be designed with other shapes as desired. It should be noted that in order to match the cell culture modules of different shapes, the cell culture carriers are also adaptable to different laying methods.

Figure 10A:
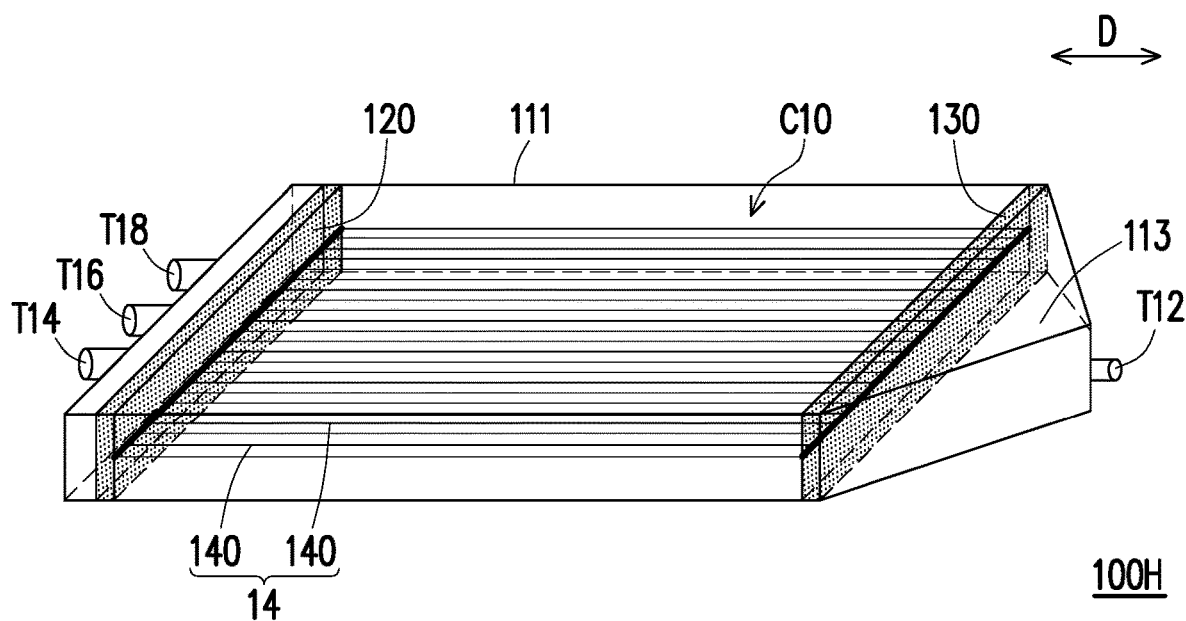
FIG. 10A and FIG. 10B are respectively schematic views of a sheet-shaped carrier member of a cell culture module in an open state and a folded state according to an exemplary embodiment.
Figure 10B:
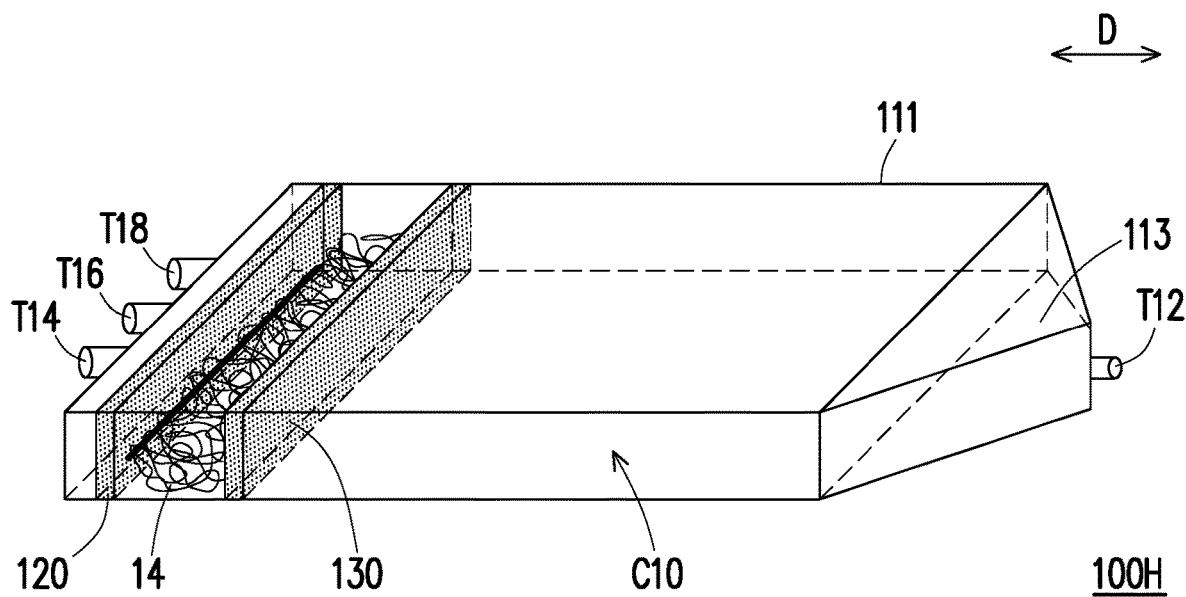

FIG. 10A and FIG. 10B are respectively schematic views of a sheet-shaped carrier member of a cell culture module in an open state and a folded state according to another exemplary embodiment. Referring to FIG. 10A and FIG. 10B, a cell culture module 100H of the present embodiment includes a casing 111, a first fixer 120, a second fixer 130 and a sheet-shaped carrier member 14. The casing 111 has a chamber C10 and at least one inlet/outlet T12, wherein the at least one inlet/outlet T12 communicates with the chamber C10. The first fixer 120 is fixed to the casing 111 and located in the chamber C10. The second fixer 130 is disposed in the chamber C10 and is movable relative to the first fixer 120. The sheet-shaped carrier member 14 is formed by arranging a plurality of cell culture carriers 140 and two opposite ends of the sheet-shaped carrier member 14 are respectively fixed to the first fixer 120 and the second fixer 130. The sheet-shaped carrier member 14 is in the open state as shown in FIG. 10A, or the sheet-shaped carrier member 14 is in the folded state as shown in FIG. 10B according to a variation in a distance between the first fixer 120 and the second fixer 130 due to a movement of the second fixer 130.

In the present embodiment, the casing 111 is a six-sided box-shaped shape, such as a flat plate shape, but is not limited thereto. When a plurality of cell culture modules 100H are used, a plurality of casings 111 may be stacked with each other to more effectively utilize the entire space. Further, the cell culture carriers 140 are designed to be arranged in the sheet-shaped carrier member 14 with a variation in the shape of the casing 111, so that the sheet-shaped carrier member 14 may be covered on one surface of the flat plate-shaped casing 111 when the sheet-shaped carrier member 14 is in the open state.

The straight strip cell culture carriers 140 may specifically be a single-line, double-line, or yarn structure and the line may be configured as a straight line, a curve, a spiral curve, a wavy curve, a zigzag curve, an inverted curve, or a sheet curve, etc., but is not limited to the above. The plurality of straight strip cell culture carriers 140 are arranged to form the sheet-shaped carrier member 14 and the cell culture carriers 140 may be arranged in a parallel arrangement or an interleaved arrangement and the arranged sheet-shaped carrier member 14 may be single-layered or multi-layered, but the disclosure is not limited thereto.

In the present embodiment, a plurality of cell culture carriers 140 are arranged in a single layer in parallel to form the sheet-shaped carrier member 14 and the cell culture carriers 140 are respectively fixed to the first fixer 120 and the second fixer 130 at two opposite ends of the axial extending direction thereof. Therefore, when the distance between the first fixer 120 and the second fixer 130A becomes less than a stretch length of the sheet-shaped carrier member 14 (or the cell culture carriers 140) due to the movement of the second fixer 130, the sheet-shaped carrier member 14 (or the cell culture carriers 140) is rendered in the folded state as shown in FIG. 10B. In this state, a plurality of cell culture carriers 140 may be used in limited space to obtain more area for cells to adhere to so as to increase the number of culturable cells. When the distance between the first fixer 120 and the second fixer 130 becomes roughly equal to the stretch length of the sheet-shaped carrier member 14 (or the cell culture carriers 140) due to the movement of the second fixer 130, the sheet-shaped carrier member 14 (or the cell culture carriers 140) is rendered in the open state as shown in FIG. 10A. The cells may be detached from the cell culture carriers 140 during a change of state of the sheet-shaped carrier member 14 from the folded state to the open state. Further, since the distance between the cell culture carriers 140 is increased, a substance such as an enzyme for facilitating detachment of the cells from the cell culture carriers 140 may be injected, and the substance may easily reach all the cells to sufficiently perform a reaction, which conduces to enhancement of a cell recovery rate.

Figure 11:
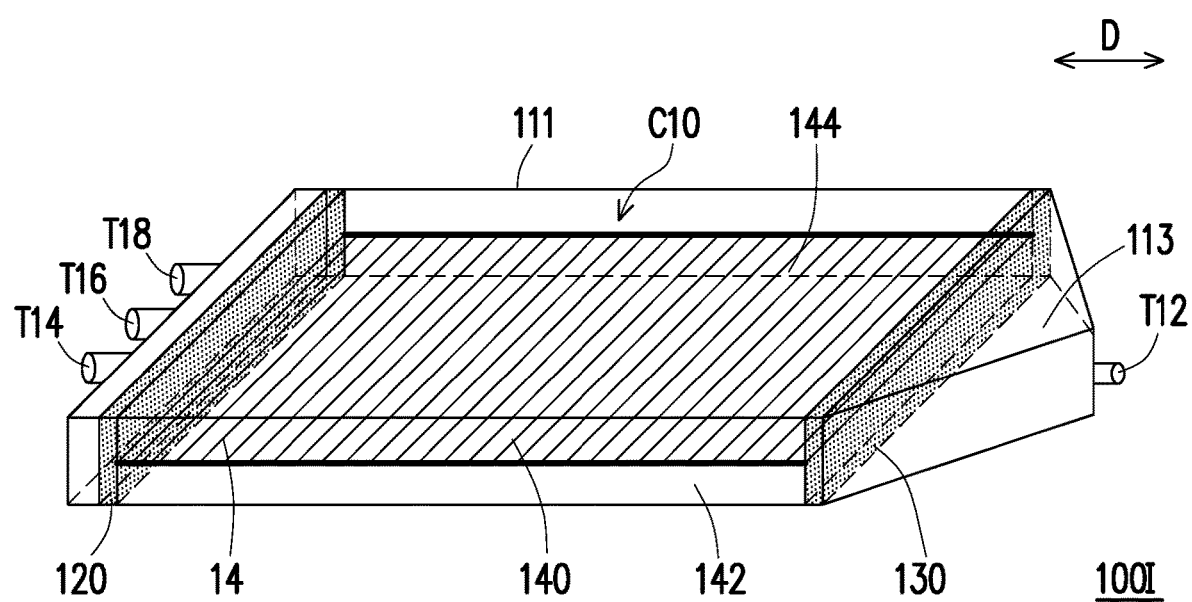
FIG. 11 is a schematic view of a cell culture module according to another exemplary embodiment.

Please refer to FIG. 11. In another exemplary embodiment, a plurality of cell culture carriers 140 are arranged in a single layer in parallel to form the sheet-shaped carrier member 14, the sheet-shaped carrier member 14 further include a first connecting portion 142 and a second connecting portion 144, and the cell culture carriers 140 are respectively fixed to the first connecting portion 142 and the second connecting portion 144 at two opposite ends of the axial extending direction thereof. The first connecting portion 142 and the second connecting portion 144 are adjacently connected to the first fixer 120 and the second fixer 130. In detail, the first connecting portion 142 and the second connecting portion 144 are two long sides of the sheet-shaped carrier member 14, and the sides in the sheet-shaped carrier member 14 fixed to the first fixer 120 and the second fixer 130 are two short sides in the sheet-shaped carrier member 14. That is, the first connecting portion 142, the second connecting portion 144, the first fixer 120 and the second fixer 130 are all located on different sides of the sheet-shaped carrier member 14.

Further, in the embodiments of FIG. 1A to FIG. 10B, a moving direction D of the second fixer is roughly parallel to the axial extending direction of the cell culture carriers 140, but in the embodiment of FIG. 11, the movement direction D of the second fixer 130 is roughly perpendicular to the axial extending direction of the cell culture carriers 140 in the sheet-shaped carrier member 14. In other exemplary embodiments, the moving direction D of the second fixer 130 is roughly at an angle to the axial extending direction of the cell culture carriers 140 in the sheet-shaped carrier member 14 and is not limited thereto.

Figure 12A:
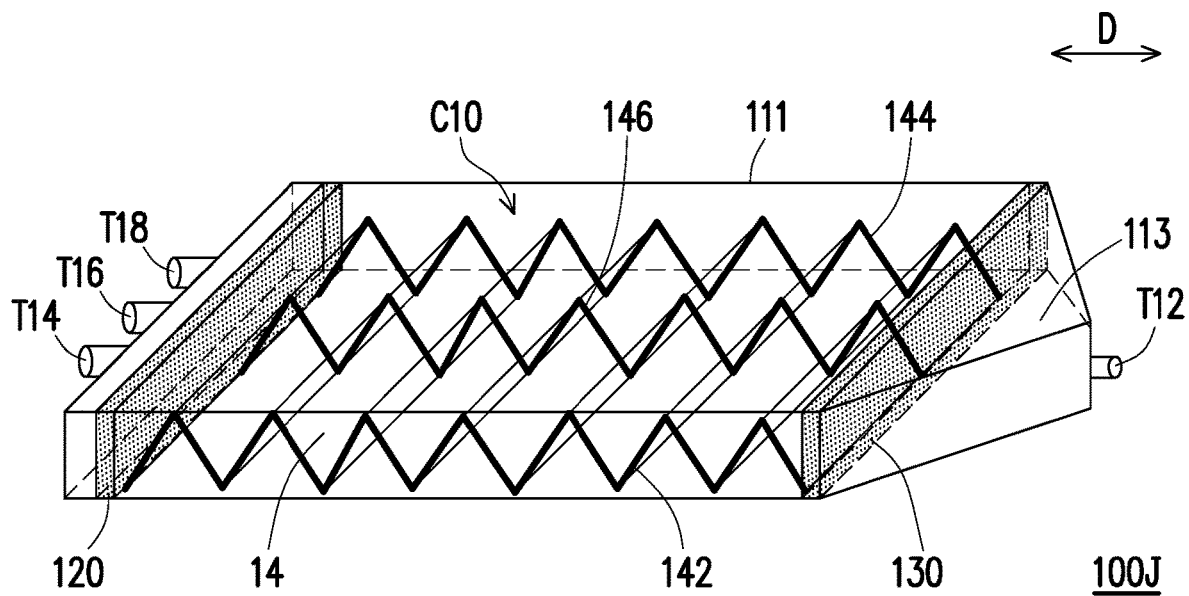
FIG. 12A and FIG. 12B are respectively schematic views of a sheet-shaped carrier member of a cell culture module in an open state and a folded state according to another exemplary embodiment.
Figure 12B:
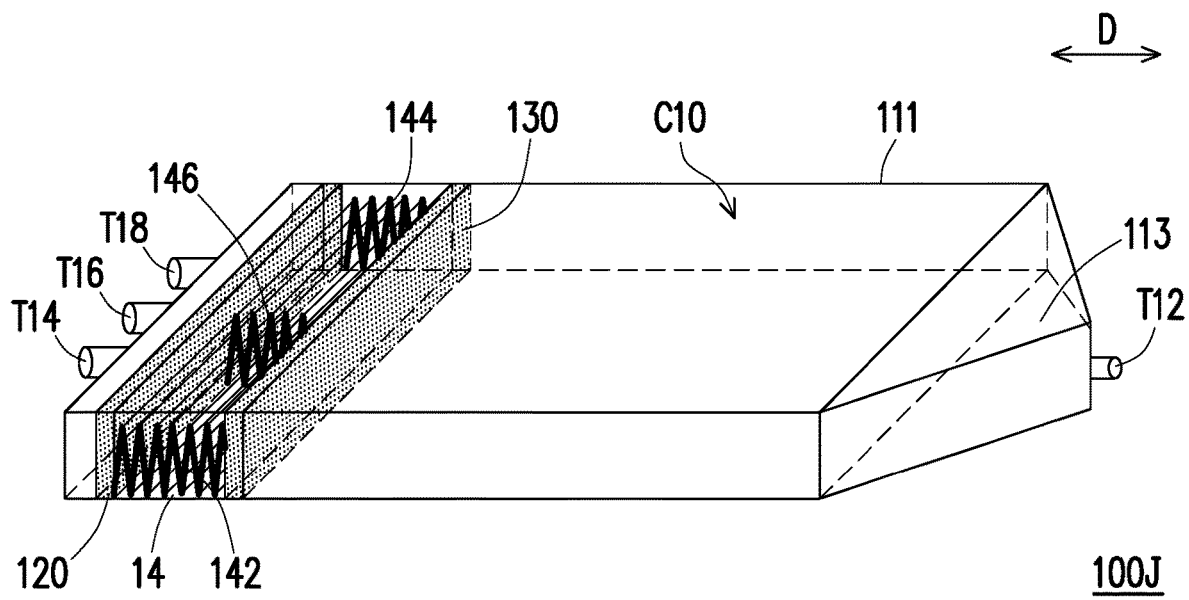

Refer to all of FIG. 11, FIG. 12A and FIG. 12B. It is noted that, in order to simplify the illustration, the cell culture carriers 140 are not illustrated in FIG. 12A and FIG. 12B, but it should be understood from the above description that the configuration of the cell culture carriers 140 may include making the axial extending direction of the cell culture carriers 140 perpendicular, angled, or parallel to the moving direction D of the second fixer 130. In the embodiment of FIG. 11, when the sheet-shaped carrier member 14 is in the open state, the first connecting portion 142 and the second connecting portion 144 are roughly straight lines or slightly curved, but in the different embodiments of FIG. 12A and FIG. 12B, the first connecting portion 142 and the second connecting portion 144 may be designed to have a zigzag or wavy shape via molding, but the disclosure is not limited thereto. The uneven shape of the first connecting portion 142 and the second connecting portion 144, such as a zigzag or a wave shape, may guide the sheet-shaped carrier member 14 to be uniformly folded and compressed when the second fixer 130 is moved toward the first fixer 120, so that when the sheet-shaped carrier member 14 is in the folded state, a suitable space exists between the plurality of cell culture carriers 140 to prevent a portion of the region between the plurality of cell culture carriers 140 from being too dense due to uneven extrusion, resulting in adverse cell growth.

As shown in FIG. 12A and FIG. 12B, the sheet-shaped carrier members 14 in a cell culture module 100J further include a third connecting portion 146. The third connecting portion 146 is disposed between the first connecting portion 142 and the second connecting portion 144, such that one end of the cell culture carriers 140 is fixed to the first connecting portion 142 and the other end of the cell culture carriers 140 is extended to the third connecting portion 146 and then extended to the second connection 144 via the third connecting portion 146. The third connecting portion 146 not only has the same shaping function as the folding guide of the first connecting portion 142 and the second connecting portion 144, when the distance between the first connecting portion 142 and the second connecting portion 144 is longer, the configuration of the third connecting portion 146 may also provide a fixed support function to prevent the cell culture carriers 140 from sagging due to the excessive distance between the two ends. In particular, the number of the third connecting portion 146 may not be limited to one.

In one exemplary embodiment, the casing 111 has a tapered portion 113 and at least one inlet/outlet T12 is disposed at the tapered portion 113. The tapered portion 113 is gradually narrowed outward from the casing 111 to form, for example, a funnel-shaped structure and the tapered portion 113 allows a cell collection fluid to easily flow out during cell collection, thereby reducing cell residue and allowing the gas remaining in the chamber C10 to be easily discharged. Of course, the tapered portion 113 may also effectively collect the fluid entering the chamber C10 to facilitate discharge.

In one exemplary embodiment, when only one single inlet/outlet T12 is disposed in the cell culture module, the inlet/outlet T12 may be used both for entry and exit of a liquid such as a culture medium and a buffer solution and for cell collection. However, in other exemplary embodiments, the entry and exit of the culture medium and the buffer solution and the cell collection may respectively use different channels, in view of preventing the whole module from contamination. In detail, the cell culture modules 100H to 100J of the present embodiment may include a plurality of inlets/outlets T12, T14, T16 and T18, wherein the inlet/outlet T12 is disposed at the tapered portion 113 and the collection of cells may be performed via the configuration of the inlet/outlet T12. The inlets/outlets T14, T16 and T18 may be disposed at the other side of the casing 111 opposite to the tapered portion 113 to respectively allow entry of different buffer solutions and culture media. It should be noted that the number of the inlets/outlets T14, T16 and T18 may be varied according to the actual type of liquid injected and is not limited to the above. In particular, the design of the relative positions of the inlet/outlet T12 and the inlets/outlets T14, T16 and T18 facilitates the distribution and flow circulation of the fluid in the chamber C10. Moreover, the cell culture modules 100H, 100I and 100J may have different designs depending on whether they are reusable. When the cell culture modules 100H, 100I and 100J are reusable, the casing 111 may be designed as two separable components, that is, the casing 111 further includes a body 112 and a cover 114, or may be further provided with a sealing member 116 (112, 114 and 116 are not shown in the figure, it may refer to FIG. 1A) and the functions and objects thereof are the same as those described above and are not repeated herein. When the cell culture modules 100H, 100I and 100J are for one time use only, the casing 111 is integrally formed and a two-piece design is unnecessary.

In addition, in the embodiments of the cell culture modules 100H, 100I and 100J, as in the aforesaid embodiments, the second fixer 130 may be may be displaced through gravity, magnetic force, or other mechanical force, thereby changing the state of the sheet-shaped carrier member 14. In detail, when gravity is configured to displace the second fixer 130, since the second fixer 130 is movably disposed in the chamber C10, when the casing 111 is placed upright, the second fixer 130 moves downward to a position close to the first fixer 120 due to its own gravity. When the sheet-shaped carrier member 14 is to be transformed into the open state, the casing 111 may be raised toward the other corresponding direction, so that the second fixer 130 moves downward to a position away from the first fixer 120 due to its own gravity and the sheet-shaped carrier member 14 is stretched by the first fixer 120 and the second fixer 130 and changed to the open state. In addition, to improve mobility of the second fixer 130, a weight block may be attached to the second fixer 130 to ensure that the second fixer 130 may move by its own gravity.

Figure 13:
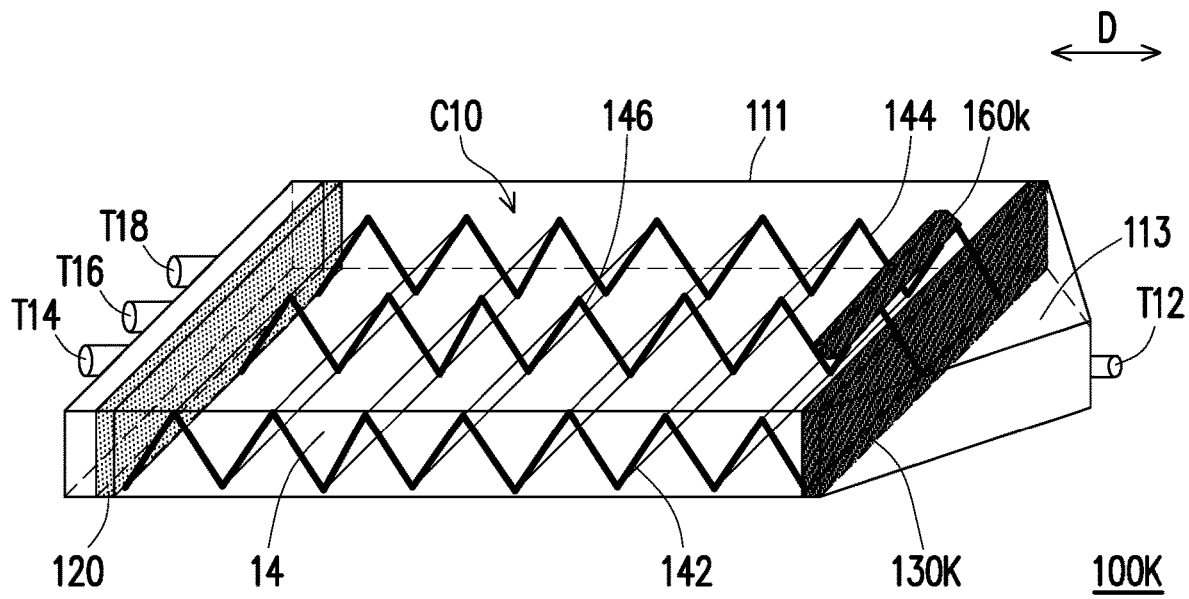
FIG. 13 is a schematic view of a cell culture module according to still another exemplary embodiment.

Referring to FIG. 13, in one exemplary embodiment, if the second fixer 130 is displaced via magnetic force, then the cell culture module 100K further includes a magnetic control part 160K. In contrast, a second fixer 130K of the present embodiment has magnetism. Therefore, the magnetic control part 160K may control the second fixer 130K to move by a magnetic force such as a magnetic attraction force or a magnetic repulsion force. When the magnetic control part 160K magnetically controls the second fixer 130K to move to a position away from the first fixer 120, the sheet-shaped carrier member 14 is in the open state. When the magnetic control part 160K controls the second fixer 130K to move to a position close to the first fixer 120, the sheet-shaped carrier member 14 is in the folded state. The shape of the magnetic control part 160K of the present embodiment is not limited as long as the magnetic control part 160K may be close to the surface of the casing 111 and the magnetic control part 160A itself is movable, thereby driving the second fixer 130K to move, but the disclosure is not limited thereto. In another exemplary embodiment, the cell culture module 100K may be placed upright to provide the second fixer 130K to assist in moving displacement due to its own weight.

Figure 14:
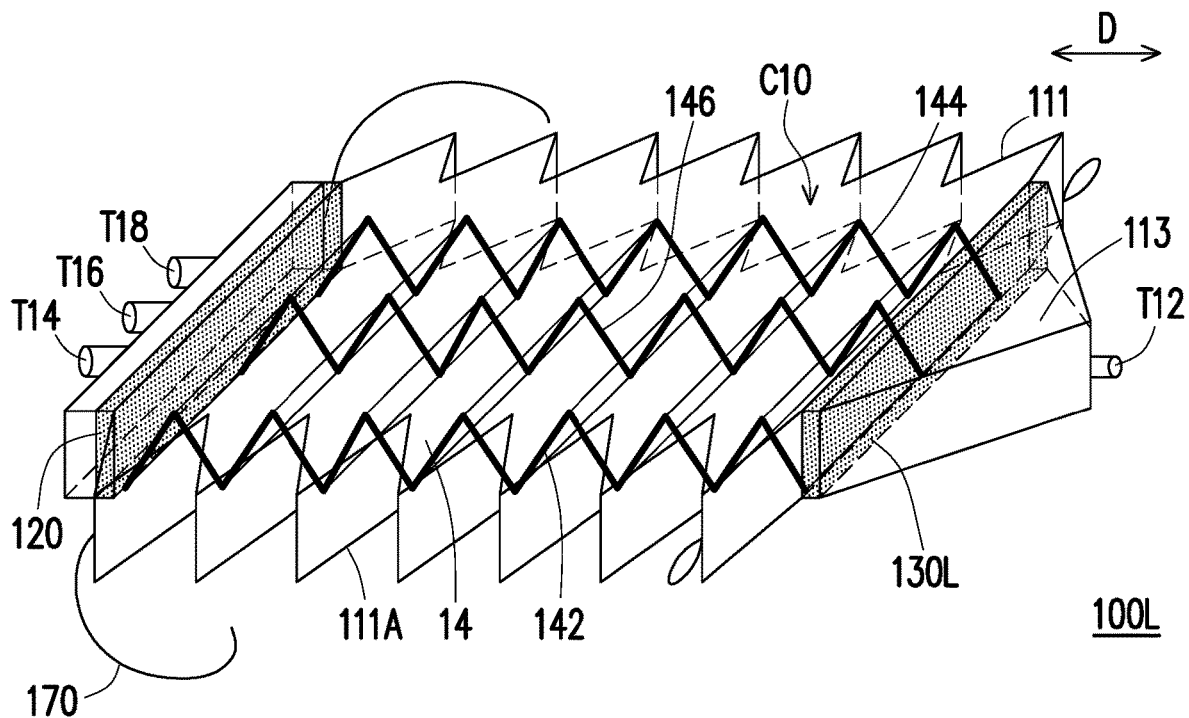
FIG. 14 is a schematic view of a cell culture module according to yet another exemplary embodiment.

Referring to FIG. 14, in one exemplary embodiment, a cell culture module 100L further includes a fastener 170. In addition, the casing 111 further has an elastic corrugated structure 111A. The elastic crease structure 111A is the same as the elastic corrugated structure 110A1 in the cell culture module 100D of FIG. 4A and FIG. 4B described above. In an unstressed state, the elastic corrugated structure 111A is, for example, the stretched state of FIG. 14. The fastener 170 is configured to control whether the elastic corrugated structure 111A maintains a compressed state or not to switch between the stretched state and the compressed state. A second fixer 130L of the present embodiment is fixed to the casing 111 and the elastic corrugated structure 111A is located between the first fixer 120 and the second fixer 130L. When the fastener 170 is fastened, the elastic corrugated structure 111A is in a compressed state and therefore the first fixer 120 and the second fixer 130L are close to each other, so that the sheet-shaped carrier member 14 is in the folded state. When the fastener 170 is unfastened, the elastic corrugated structure 111A is in the stretched state and therefore the first fixer 120 and the second fixer 130L are away from each other, so that the sheet-shaped carrier member 14 is in the open state. It should be noted that although the fastener 170 is taken as an example in the present embodiment, the fastener 170 may also be arbitrarily replaced with other fixers, such as a velcro, a screw, a rope and the like.

Figure 15:
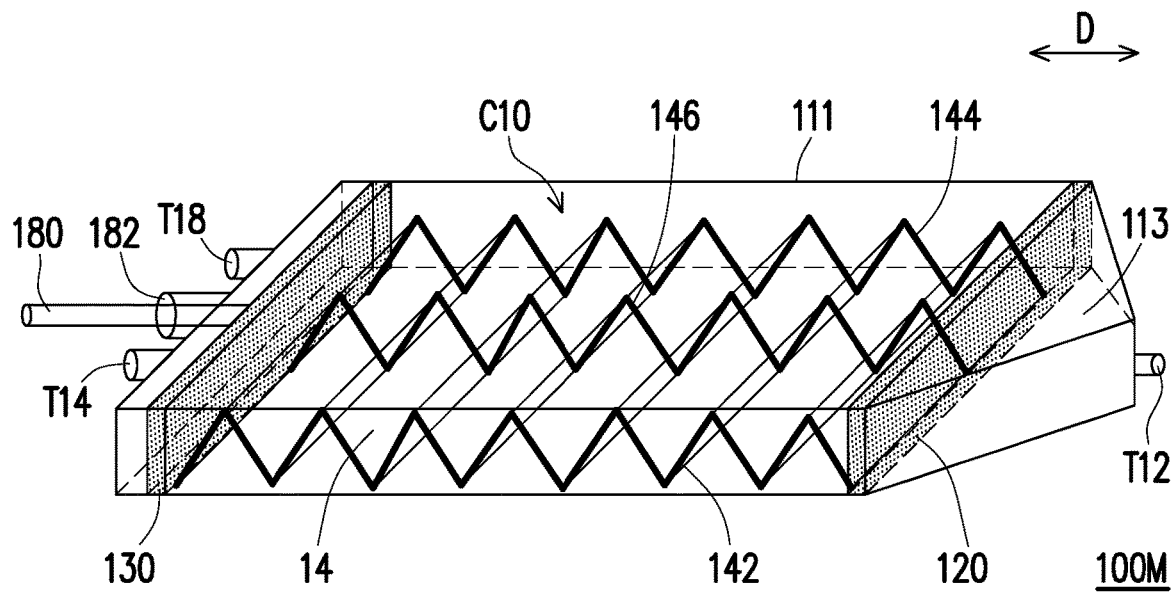
FIG. 15 is a schematic view of a cell culture module according to an exemplary embodiment.

Referring to FIG. 15, in one exemplary embodiment, a cell culture module 100M is similar to the cell culture module 100E of FIG. 5 and further includes a rod 180 and a guide hole 182. The guide hole 182 is located at one end of the casing 111 opposite to the first fixer 120 to guide the rod 180 to movably penetrate the casing 111. The rod 180 is connected to the second fixer 130 to control the second fixer 130 to move. By controlling the degree of stretch of the rod 180 into the casing 111, the second fixer 130B may be controlled to move to a position close to or away from the first fixer 120. It should be noted that in the present embodiment, the second fixer 130 and the tapered portion 113 are located at corresponding different sides of the casing 111, but in other exemplary embodiments, the second fixer 130 and the tapered portion 113 may be at the same side of the casing 111 (i.e., the rod 180 and the guide hole 182 are disposed at the same side as the tapered portion 113), but the disclosure is not limited thereto.

Figure 16:
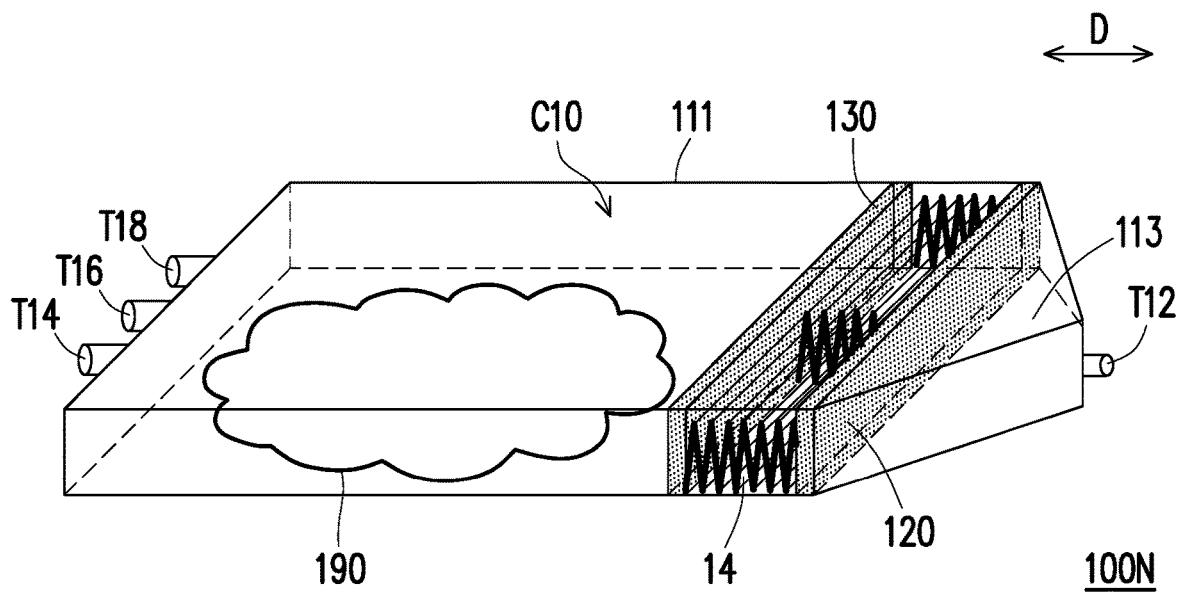
FIG. 16 is a schematic view of a cell culture module according to another exemplary embodiment.

Referring to FIG. 16, in one exemplary embodiment, a cell culture module 100N is similar to the cell culture module 100F of FIG. 6 and further includes a fluid pressure control part 190 disposed at the casing 111 and located in the chamber C10. The second fixer 130 is located between the fluid pressure control part 190 and the first fixer 120. The fluid pressure control part 190 is configured to control the second fixer 130 to move. For example, the fluid pressure control part 190 is applicable to bags for containing fluids. However, the disclosure is not limited thereto. As a gas, water, oil or other fluid contained in the fluid pressure control part 190 increases, the volume of the fluid pressure control part 190 also increases, thus pushing the second fixer 130 to move in a direction approaching the first fixer 120. As the gas, water, oil or other fluid contained in the fluid pressure control part 190 decreases, the volume of the fluid pressure control part 190 also decreases, thus allowing the second fixer 130 to move in a direction away from the first fixer 120. In the present embodiment, the second fixer 130 and the tapered portion 113 are located at corresponding different sides of the casing 111, but in other exemplary embodiments, the second fixer 130 and the tapered portion 113 may be at the same side of the casing (i.e., the fluid pressure control part 190 is disposed at the same side as the tapered portion 113), but the disclosure is not limited thereto.

Figure 17:
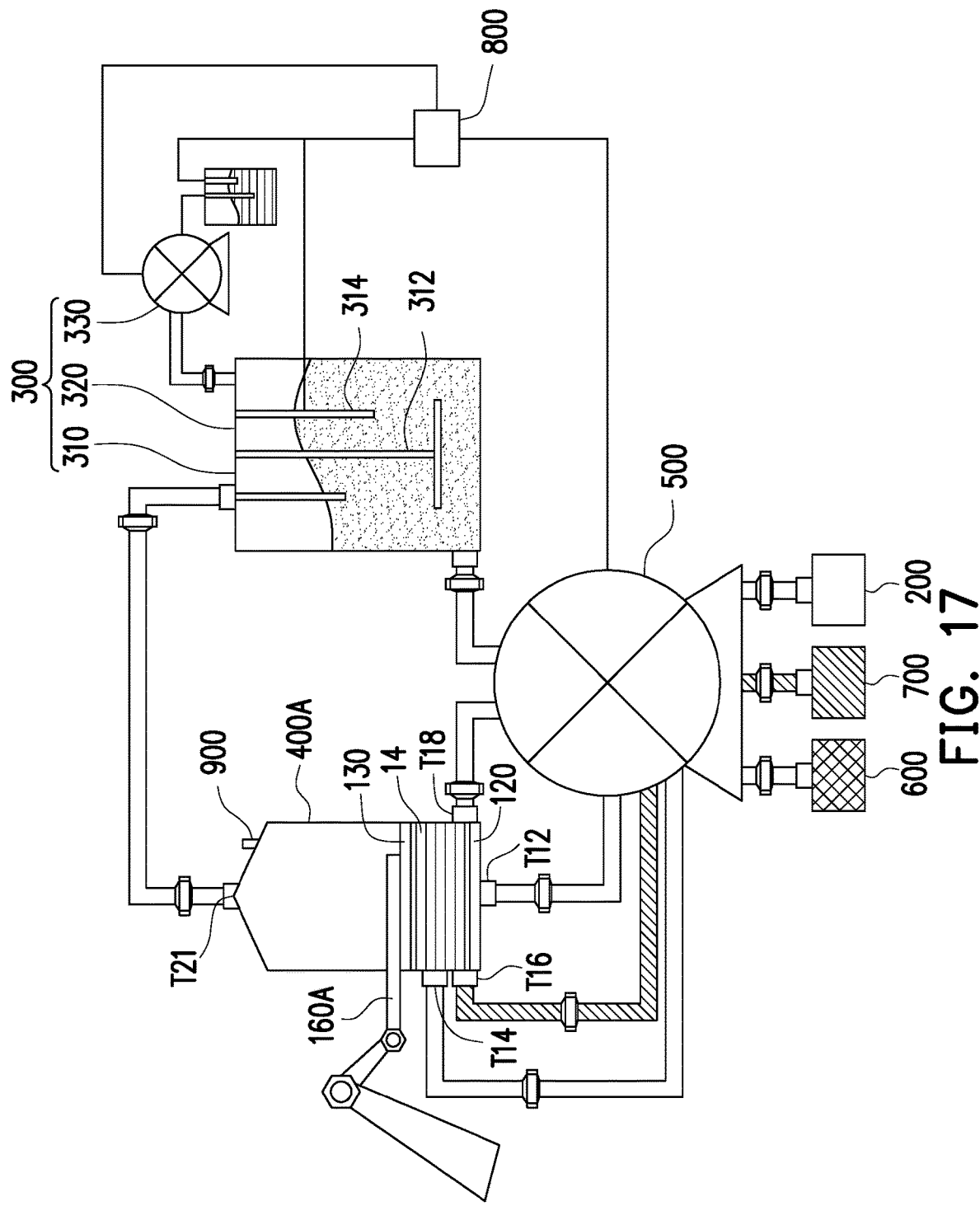
FIG. 17 is a schematic view of a cell culture system according to an exemplary embodiment.

FIG. 17 is a schematic of a cell culture system according to another exemplary embodiment. A cell culture system 2000 of the present embodiment includes a cell tank 200, a culture medium module 300 and a cell culture module 400A. The cell tank 200 and the culture medium module 300 respectively communicate with the cell culture module 400A. The cell culture module 400A may be the cell culture module of each of the foregoing embodiments (such as the cell culture modules 100H to 100N) or other cell culture modules conforming to the spirit according to one or more exemplary embodiments and a detailed description of the cell culture module 400A is omitted herein. Since a cell culture system 2000 of the present embodiment adopts the same cell culture module 400A as the cell culture module of each of the foregoing embodiments, the cell culture system 2000 of the present embodiment may increase the yield and recovery rate of the cell culture. In addition, the cell culture system 2000 of the present embodiment may optionally further include a pump 500, a cleaning solution tank 600, a cell detachment enzyme tank 700 and a controller 800. The cell tank 200 and the culture medium module 300 respectively communicate with the cell culture module 400A via the pump 500. The cleaning solution tank 600 and the cell detachment enzyme tank 700 also both communicate with the cell culture module 400A, such as communicate with the cell culture module 400A via the pump 500. The controller 800 is connected to the cell tank 200, the cleaning solution tank 600, the cell detachment enzyme tank 700, the cell culture module 400A and the culture medium module 300 respectively via the pump 500, the culture medium sensor 314 and the pump 320 to control the pump 500, the pump 320, the regulator 330 and the culture medium sensor 314.

When performing cell culture, first, the cells to be cultured are attached to the sheet-shaped carrier member 14 in the folded state. In detail, the sheet-shaped carrier member 14 of the cell culture module 400A may be first in the folded state and the configuration of each pipeline of the system may be completed. In particular, the method of configuration of the sheet-shaped carrier member 14 of the cell culture module 400A in the folded state includes moving the second fixer 130 to a position close to the first fixer 120. However, the method is not limited thereto and as in the foregoing embodiments, the second fixer 130 may be displaced by gravity, magnetic force, or other mechanical force, which is not repeated herein. Next, the cells to be cultured in the cell tank 200 are sent to the cell culture module 400A using the pump 500 to inoculated the cells to be cultured on the sheet-shaped carrier member 14 in the folded state. In other exemplary embodiments, when the sheet-shaped carrier member 14 of the cell culture module 400A are in the open state, each pipeline of the system is first configured and then the cells are inoculated on the sheet-shaped carrier member 14 in the open state. Then, the sheet-shaped carrier member 14 of the cell culture module 400A is rendered into the folded state for subsequent cell culture steps, but the disclosure is not limited to the above.

After the cells are attached, a culture medium is perfused and circulated in the cell culture module 400A and a cell culture is started. Next, the culture medium is discharged and a cleaning solution is perfused and then the remaining culture medium is removed by immersion and cleaning.

Next, a cell detachment enzyme is perfused such that the sheet-shaped carrier member 14 and the cells are immersed therein and when the sheet-shaped carrier member 14 is in the open state, the cells are desorbed from the sheet-shaped carrier member 14 and suspended in the suspension of the cell culture module 400A. In detail, in one exemplary embodiment, the cell desorbing enzyme may be perfused first and then the sheet-shaped carrier member 14 is loosened from the folded state and transformed into the open state of a two-dimensional structure. In other exemplary embodiments, the sheet-shaped carrier member 14 may also first be loosened from the folded state and transformed into the open state of a two-dimensional structure and then the cell detachment enzyme is perfused, but the disclosure is not limited to the above.

Lastly, the suspension containing the cells is collected. The detailed operation steps are the same as those of the foregoing cell culture system 1000 and are not repeated herein.

As mentioned above, in the cell culture module and cell culture system in the present embodiment, since the second fixer is movable, the sheet-shaped carrier member may switch between the open state and the folded state according to a variation in a distance between the first fixer and the second fixer at two ends of the sheet-shaped carrier member. The sheet-shaped carrier member in the folded state helps to increase the yield of the cell culture, and the sheet-shaped carrier member in the open state may improve the cell recovery rate and the quality of the collected cells.

It should be noted that in the disclosure, when the cell culture carriers are in the untwisted/twisted state and the sheet-shaped carrier member is in the open/folded state, the cell growth region created by the plurality of cell culture carriers is roughly changed between a two-dimensional surface state/three-dimensional space, which is intended to be described in terms of the different laying methods of the cell culture carriers, but the disclosure is not limited thereto.

It will be apparent to those skilled in the art that various modifications and variations may be made to the structure of the disclosed embodiments without departing from the scope or spirit according to one or more exemplary embodiments. In view of the foregoing, it is intended that the disclosure cover modifications and variations of this disclosure provided they fall within the scope of the following claims and their equivalents.

What is claimed is:

1. A cell culture module, comprising:
   a casing having a chamber and at least one inlet/outlet, wherein the at least one inlet/outlet communicates with the chamber;
   a first fixer fixed to the casing and located in the chamber;
   a second fixer disposed in the chamber and being movable relative to the first fixer; and
   a sheet-shaped carrier member formed by arranging a plurality of cell culture carriers, wherein two opposite ends of the sheet-shaped carrier member are respectively fixed to the first fixer and the second fixer, and the sheet-shaped carrier member is in an open state or a folded state according to a variation in a distance between the first fixer and the second fixer due to a movement of the second fixer,
   wherein a moving direction of the second fixer is perpendicular to an axial extending direction of the plurality of cell culture carriers in the sheet-shaped carrier member.

2. The cell culture module according to claim 1, wherein the plurality of cell culture carriers are respectively fixed to the first fixer and the second fixer at two opposite ends of the axial extending direction.

3. The cell culture module according to claim 1, wherein the sheet-shaped carrier member further comprises a first connecting portion and a second connecting portion, two opposite ends of the plurality of cell culture carriers are respectively fixed to the first connecting portion and the second connecting portion, and the first connecting portion and the second connecting portion are adjacently connected to the first fixer and the second fixer.

4. The cell culture module according to claim 3, wherein the first connecting portion and the second connecting portion have a zigzag or wavy shape.

5. The cell culture module according to claim 3, wherein the sheet-shaped carrier member further comprises a third connecting portion disposed between the first connecting portion and the second connecting portion, such that one end of the plurality of cell culture carriers is fixed to the first connecting portion and another end of the plurality of cell culture carriers is extended to the third connecting portion and then extended to the second connecting portion via the third connecting portion.

6. The cell culture module according to claim 1, wherein the casing has a tapered portion and the at least one inlet/outlet is disposed at the tapered portion.

7. The cell culture module according to claim 1, wherein the casing has a tapered portion, and a number of the at least one inlet/outlet is plural and the inlets/outlets are respectively disposed at the tapered portion and another side of the casing opposite to the tapered portion.

8. The cell culture module according to claim 1, further comprising a magnetic control part, wherein the second fixer has magnetism and the magnetic control part is configured to magnetically control the second fixer to move.

9. The cell culture module according to claim 1, further comprising a fixer, wherein the casing further has an elastic corrugated structure, the fixer is configured to control the elastic corrugated structure to switch between a stretched state and a compressed state, the second fixer is fixed to the casing and the elastic corrugated structure is located between the first fixer and the second fixer,
   when the elastic corrugated structure is in the stretched state, the sheet-shaped carrier member is in the open state, and
   when the elastic corrugated structure is in the compressed state, the sheet-shaped carrier member is in the folded state.

10. The cell culture module according to claim 1, further comprising a rod movably inserted through the casing and connected to the second fixer to control the second fixer to move.

11. The cell culture module according to claim 1, further comprising a fluid pressure control part disposed at the casing and located in the chamber, wherein the second fixer is located between the fluid pressure control part and the first fixer and the fluid pressure control part is configured to control the second fixer to move.

12. A cell culture system, comprising:
    a cell tank;
    a culture medium module; and
    a cell culture module according to claim 1, wherein the cell tank and the culture medium module respectively communicate with the cell culture module.

13. The cell culture system according to claim 12, further comprising a pump, wherein the cell tank and the culture medium module respectively communicates with the cell culture module via the pump.

14. The cell culture system according to claim 12, further comprising a cleaning solution tank communicated with the cell culture module.

15. The cell culture system according to claim 12, further comprising a cell detachment enzyme tank communicated with the cell culture module.

16. The cell culture system according to claim 12, further comprising a controller, wherein the controller is connected to the cell tank, the culture medium module and the cell culture module.

17. The cell culture system according to claim 12, wherein in the cell culture module, the plurality of cell culture carriers are respectively fixed to the first fixer and the second fixer at two opposite ends of the axial extending direction of the plurality of cell culture carriers.

18. The cell culture system according to claim 12, wherein in the cell culture module, the sheet-shaped carrier member further comprises a first connecting portion and a second connecting portion, two opposite ends of the plurality of cell culture carriers are respectively fixed to the first connecting portion and the second connecting portion, and the first connecting portion and the second connecting portion are adjacently connected to the first fixer and the second fixer.

19. The cell culture system according to claim 18, wherein in the cell culture module, the first connecting portion and the second connecting portion have a zigzag or wavy shape.

20. The cell culture system according to claim 18, wherein in the cell culture module, the sheet-shaped carrier member further comprises a third connecting portion disposed between the first connecting portion and the second connecting portion, such that one end of the plurality of cell culture carriers is fixed to the first connecting portion and another end of the plurality of cell culture carriers is extended to the third connecting portion and then extended to the second connecting portion via the third connecting portion.

21. The cell culture system according to claim 12, wherein in the cell culture module, the casing has a tapered portion and the at least one inlet/outlet is disposed at the tapered portion.

22. The cell culture system according to claim 12, wherein the casing has a tapered portion, and in the cell culture module, a number of the at least one inlet/outlet is plural and the inlets/outlets are respectively disposed at the tapered portion and the other side of the casing opposite to the tapered portion.

23. The cell culture system according to claim 12, wherein the cell culture module further comprises a magnetic control part, the second fixer has magnetism, and the magnetic control part is configured to magnetically control the second fixer to move.

24. The cell culture system according to claim 12, wherein the cell culture module further comprises a fixer, the casing further has an elastic corrugated structure, the fixer is configured to control the elastic corrugated structure to switch between a stretched state and a compressed state, the second fixer is fixed to the casing and the elastic corrugated structure is located between the first fixer and the second fixer, when the elastic corrugated structure is in the stretched state, the sheet-shaped carrier member is in the open state, and when the elastic corrugated structure is in the compressed state, the sheet-shaped carrier member is in the folded state.

25. The cell culture system according to claim 12, wherein the cell culture module further comprises a rod movably inserted through the casing and connected to the second fixer to control the second fixer to move.

26. The cell culture system according to claim 12, wherein the cell culture module further comprises a fluid pressure control part disposed at the casing and located in the chamber, the second fixer is located between the fluid pressure control part and the first fixer, and the fluid pressure control part is configured to control the second fixer to move.

27. A cell culture method adopting the cell culture module according to claim 1, comprising the steps of:
attaching cells on the sheet-shaped carrier member in the folded state;
perfusing and circulating a culture medium in the cell culture module and starting a cell culture;
discharging the culture medium and perfusing a cleaning solution and performing an immersion and cleaning to remove a remaining culture medium;
perfusing a cell detachment enzyme, and when the sheet-shaped carrier member is in the open state, desorbing the cells from the sheet-shaped carrier member to be suspended in a suspension of the cell culture module; and
collecting the suspension containing the cells.

28. The cell culture method according to claim 27, wherein the step of attaching the cells to the sheet-shaped carrier member in the folded state further comprises: rendering the sheet-shaped carrier member of the cell culture module to the folded state first and then inoculating the cells on the sheet-shaped carrier member in the folded state.

29. The cell culture method according to claim 27, wherein the step of attaching the cells on the sheet-shaped carrier member in the folded state further comprises: inoculating the cells on the sheet-shaped carrier member in the open state and rendering the sheet-shaped carrier member of the cell culture module to the folded state.

30. The cell culture method according to claim 27, wherein the step of attaching the cells on the sheet-shaped carrier member in the folded state further comprises: moving the second fixer to a position close to the first fixer, so that the sheet-shaped carrier member of the cell culture module is in the folded state.

31. The cell culture method according to claim 27, wherein the step of perfusing the cell detachment enzyme and desorbing the cells from the sheet-shaped carrier member to be suspended in the suspension of the cell culture module when the sheet-shaped carrier member is in the open state further comprises: perfusing the cell detachment enzyme first and then transforming the sheet-shaped carrier member from the folded state to the open state.

32. The cell culture method according to claim 27, wherein the step of perfusing the cell detachment enzyme and desorbing the cells from the sheet-shaped carrier member to be suspended in the suspension of the cell culture module when the sheet-shaped carrier member is in the open state further comprises: transforming the sheet-shaped carrier member from the folded state to the open state first and then perfusing the cell detachment enzyme.

* * * * *